United States Patent
Reitmeir et al.

(10) Patent No.: US 9,677,107 B2
(45) Date of Patent: Jun. 13, 2017

(54) METHOD FOR PRODUCING A RECOMBINANT PROTEIN OF INTEREST BY USING THE N$^{pro}$ TECHNOLOGY

(71) Applicants: Sandoz AG, Basel (CH); Boehringer Ingelheim RCV GmbH & Co KG, Vienna (AT)

(72) Inventors: Maria Reitmeir, Häring (AT); Rainer Schneider, Wörgl (AT); Bernhard Auer, Innsbruck (AT)

(73) Assignees: SANDOZ AG, Basel (CH); BOEHRINGER INGELHEIM RCV GMBH & CO KG, Vienna (AT)

(*) Notice: Subject to any disclaimer, the term of this patent is extended or adjusted under 35 U.S.C. 154(b) by 0 days.

(21) Appl. No.: 14/135,389

(22) Filed: Dec. 19, 2013

(65) Prior Publication Data

US 2014/0170702 A1 Jun. 19, 2014

(30) Foreign Application Priority Data

Dec. 19, 2012 (EP) .................................... 12198006

(51) Int. Cl.
  *C12P 21/06* (2006.01)
  *C12N 15/70* (2006.01)
  *C12P 21/02* (2006.01)
  *C12N 9/50* (2006.01)

(52) U.S. Cl.
  CPC .............. *C12P 21/06* (2013.01); *C12N 9/506* (2013.01); *C12N 15/70* (2013.01); *C12P 21/02* (2013.01); *C07K 2319/50* (2013.01)

(58) Field of Classification Search
  CPC ................... C12P 21/06; C07K 1/00
  See application file for complete search history.

(56) References Cited

FOREIGN PATENT DOCUMENTS

| WO | WO 01/11056 A1 | 2/2001 |
|---|---|---|
| WO | WO 01/11057 A1 | 2/2001 |
| WO | WO 2006/113957 A2 | 11/2006 |
| WO | WO 2006/113958 A2 | 11/2006 |
| WO | WO 2006/113959 A2 | 11/2006 |

OTHER PUBLICATIONS

Ruggli et al, Classical Swine Fever Virus Can Remain Virulent after Specific Elimination of the Interferon Regulatory Factor 3-Degrading Function of Npro. Journal of Virology, Jan. 2009, vol. 83, No. 2 p. 817-829.*

Walther et al, Getting ready for PAT: Scale up and inline monitoring of protein refolding of Npro fusion proteins. Process Biochemistry 49 (2014) 1113-1121.*

Achmüller et al., "Npro fusion echnology to produce proteins with authentic N termini in *E. coli*," Nature Methods, vol. 4, No. 12, Dec. 2007 (Published online: Nov. 18, 2007), pp. 1037-1043, XP02663733.

Dürauer et al., "Npro Autoprotease Fusion Technology: Development, Characteristics, and Influential Factors," Separation Science and Technology, vol. 45, 2010, pp. 2194-2209, XP009166982.

Ferrer-Miralles et al., "Microbial factories for recombinant pharmaceuticals," Microbial Cell Factories, vol. 8, No. 17, Mar. 24, 2009, pp. 1-8.

Hahn et al., "Peptide affinity chromatography media that bind N(pro) fusion proteins under chaotropic conditions," Journal of Chromatography A, vol. 1217, 2010 (Available online Aug. 11, 2010), pp. 6203-6213, XP027289138.

Kaar et al., "Refolding of Npro Fusion Proteins," Biotechnology and Bioengineering, vol. 104, No. 4, Nov. 1, 2009 (Published online Jun. 4, 2009), pp. 774-784, XP055050976.

Li, "Self-cleaving fusion tags for recombinant protein production," Biotechnol. Lett, vol. 33, 2011(published online: Jan. 26, 2011), pp. 869-881, XP055052800.

Schmoeger et al., "Matrix-assisted refolding of autoprotease fusion proteins on an ion exchange column: A kinetic investigation," Journal of Chromatography A, vol. 1217, 2010 (Available online Jul. 22, 2010), pp. 5950-5956, XP027236223.

Ueberbacher et al., "Eddie fusion proteins: Triggering autoproteolytic cleavage," Process Biochemistry, vol. 44, 2009 (Accepted: Jun. 23, 2009), pp. 1217-1224, XP026614237.

Vallejo et al., "Strategies for the recovery of active proteins through refolding of bacterial inclusion body proteins," Microbial Cell Factories, vol. 3, No. 11, 2004 (Published: Sep. 2, 2004), pp. 1-12.

Xing et al., "Streamlined protein expression and purification using cleavable self-aggregating tags," Microbial Cell Factories, vol. 10, No. 42, 2011, pp. 1-7, XP055052801.

Database UniProtKB Sequence/Annotation (UniSave), retrieved from EBI accession No. UNIPROT:M9T861, Jun. 26, 2013, 2 pages, XP002719436.

Database UniProtKB Sequence/Annotation (UniSave), retrieved from EBI accession No. UNIPROT:Q5L4B1, Feb. 1, 2005, 1 page, XP002692351.

Cedillo Rosales S et al., Accession No. Q5L4B1, Definition:N$^{pro}$, Uniprot [online], 2005, <http://www.uniprot.org/uniprot/Q5L4B1> [retrieved on Jul. 21, 2016].

(Continued)

*Primary Examiner* — Sheridan Swope
(74) *Attorney, Agent, or Firm* — Birch, Stewart, Kolasch & Birch, LLP

(57) ABSTRACT

Disclosed is a method for producing a recombinant protein of interest, the method being characterized in by the following steps:
(a) providing a fusion protein comprising an N$^{pro}$ autoprotease moiety and a protein of interest moiety in inclusion bodies,
(b) solubilizing the inclusion bodies,
(c) allowing the fusion protein to be cleaved by the N$^{pro}$ autoprotease moiety under chaotropic conditions, wherein the recombinant protein of interest is cleaved from the fusion protein and wherein the recombinant protein of interest is not yet renatured or simultaneously renatured, and
(d) recovering the protein of interest, optionally including a renaturing step for the protein of interest.

36 Claims, 7 Drawing Sheets
(5 of 7 Drawing Sheet(s) Filed in Color)

(56) References Cited

OTHER PUBLICATIONS

Japanese Office Action and English Translation for JP Patent Application No. 2015-548587 mailed Aug. 2, 2016.
Kaar et al., "Refolding of $N^{pro}$ fusion proteins" Biotechnol. Bioeng., 2009, vol. 104, No. 4, pp. 774-784.
Protein Science Society of Japan, Archives [online], 2008, e041,<http://www.pssj.jp/archives/files/articles/041.pdf> [retrieved on Jul. 20, 2016] (cited to show well-known techniques).
Ruggli et al., "Classical Swine Fever Virus Can Remain Virulent after Specific Elimination of the Interferon Regulatory Factor 3-Degrading Function of $N^{pro\Delta}$" J. Virol., 2009, vol. 83, No. 2, pp. 817-829.

\* cited by examiner

SEQUENCE LISTING

<160> NUMBER OF SEQ ID NOS: 12

<210> SEQ ID NO 1
<211> LENGTH: 148
<212> TYPE: PRT
<213> ORGANISM: CSFV

<400> SEQUENCE: 1

Met Glu Pro Leu Tyr Asp Lys Asn Gly Ala Val Leu Phe Gly Glu Pro
1               5                   10                  15

Ser Asp Thr His Pro Gln Ser Thr Leu Lys Leu Pro His Pro Arg Gly
                20                  25                  30

Glu Lys Glu Val Ile Val Gly Ile Arg Asp Leu Pro Arg Lys Gly Asp
            35                  40                  45

Cys Arg Thr Gly Asn Arg Leu Gly Pro Val Ser Gly Leu Phe Val Lys
        50                  55                  60

Pro Gly Pro Val Phe Tyr Gln Asp Tyr Ser Gly Pro Val Tyr His Arg
65                  70                  75                  80

Ala Pro Leu Glu Gln Phe Lys Gln Ala Pro Met Cys Glu Val Thr Lys
                85                  90                  95

Arg Ile Gly Arg Val Thr Gly Ser Asp Gly Asn Leu Tyr His Met Tyr
            100                 105                 110

```
Val Cys Thr Asp Gly Cys Ile Leu Val Lys Thr Ala Lys Arg Glu Gly
        115                 120                 125

Gln Asp Val Leu Lys Trp Val Tyr Asn Val Leu Asp Ser Pro Ile Trp
130                 135                 140

Val Thr Ser Cys
145

<210> SEQ ID NO 2
<211> LENGTH: 168
<212> TYPE: PRT
<213> ORGANISM: CSFV

<400> SEQUENCE: 2

Met Glu Leu Leu Asn Phe Glu Leu Leu Tyr Lys Thr Tyr Lys Gln Lys
1               5                   10                  15

Pro Ala Gly Val Gln Glu Pro Leu Tyr Asp Lys Asn Gly Ala Val Leu
            20                  25                  30

Phe Gly Glu Pro Ser Asp Thr His Pro Gln Ser Thr Leu Lys Leu Pro
        35                  40                  45

His Pro Arg Gly Glu Lys Glu Val Ile Val Gly Ile Arg Asp Leu Pro
    50                  55                  60

Arg Lys Gly Asp Cys Arg Thr Gly Asn Arg Leu Gly Pro Val Ser Gly
65                  70                  75                  80

Leu Phe Val Lys Pro Gly Pro Val Phe Tyr Gln Asp Tyr Ser Gly Pro
                85                  90                  95

Val Tyr His Arg Ala Pro Leu Glu Gln Phe Lys Gln Ala Pro Met Cys
            100                 105                 110

Glu Val Thr Lys Arg Ile Gly Arg Val Thr Gly Ser Asp Gly Asn Leu
        115                 120                 125

Tyr His Met Tyr Val Cys Thr Asp Gly Cys Ile Leu Val Lys Thr Ala
    130                 135                 140

Lys Arg Glu Gly Gln Asp Val Leu Lys Trp Val Tyr Asn Val Leu Asp
145                 150                 155                 160

Ser Pro Ile Trp Val Ala Ser Cys
                165

<210> SEQ ID NO 3
<211> LENGTH: 16
<212> TYPE: PRT
<213> ORGANISM: Artificial Sequence
<220> FEATURE:
<223> OTHER INFORMATION: model peptide termed pep6His

<400> SEQUENCE: 3

Ser Val Asp Lys Leu Ala Ala Ala Leu Glu His His His His His His
1               5                   10                  15

<210> SEQ ID NO 4
<211> LENGTH: 224
<212> TYPE: PRT
<213> ORGANISM: CSFV

<400> SEQUENCE: 4

Met Glu Pro Leu Tyr Asp Lys Asn Gly Ala Val Leu Phe Gly Glu Pro
1               5                   10                  15

Ser Asp Thr His Pro Gln Ser Thr Leu Lys Leu Pro His Pro Arg Gly
            20                  25                  30

Glu Asp Glu Val Glu Val Gly Ile Arg Asp Leu Pro Arg Lys Gly Asp
```

```
                35                  40                  45
Cys Arg Thr Gly Asn Arg Leu Gly Pro Val Ser Gly Leu Phe Val Lys
 50                  55                  60

Pro Gly Pro Val Phe Tyr Gln Asp Tyr Ser Gly Pro Val Tyr His Arg
 65                  70                  75                  80

Ala Pro Leu Glu Gln Phe Lys Gln Thr Pro Met Glu Thr Thr Lys
                 85                  90                  95

Arg Ile Gly Arg Val Thr Gly Ser Asp Gly Asn Leu Tyr His Met Tyr
                100                 105                 110

Val Glu Thr Asp Gly Glu Ile Leu Val Lys Gln Ala Lys Arg Glu Gly
                115                 120                 125

Gln Asp Val Leu Lys Trp Thr Tyr Asn Thr Leu Asp Ser Pro Ile Trp
130                 135                 140

Val Thr Ser Cys Gln Pro Asp Ala Ile Asn Ala Pro Val Thr Cys Cys
145                 150                 155                 160

Tyr Asn Phe Thr Asn Arg Lys Ile Ser Val Gln Arg Leu Ala Ser Tyr
                165                 170                 175

Arg Arg Ile Thr Ser Ser Lys Cys Pro Lys Glu Ala Val Ile Phe Lys
                180                 185                 190

Thr Ile Val Ala Lys Glu Ile Cys Ala Asp Pro Lys Gln Lys Trp Val
                195                 200                 205

Gln Asp Ser Met Asp His Leu Asp Lys Gln Thr Gln Thr Pro Lys Thr
210                 215                 220

<210> SEQ ID NO 5
<211> LENGTH: 224
<212> TYPE: PRT
<213> ORGANISM: CSFV

<400> SEQUENCE: 5

Met Glu Pro Val Tyr Asp Thr Ala Gly Arg Pro Leu Phe Gly Asn Pro
 1               5                   10                  15

Ser Glu Val His Pro Gln Ser Thr Leu Lys Leu Pro His Asp Arg Gly
                20                  25                  30

Glu Asp Asp Ile Glu Thr Thr Leu Arg Asp Leu Pro Arg Lys Gly Asp
                35                  40                  45

Cys Arg Ser Gly Asn His Leu Gly Pro Val Ser Gly Ile Tyr Ile Lys
 50                  55                  60

Pro Gly Pro Val Tyr Tyr Gln Asp Tyr Thr Gly Pro Val Tyr His Arg
 65                  70                  75                  80

Ala Pro Leu Glu Phe Phe Asp Glu Thr Gln Phe Glu Gly Thr Thr Lys
                 85                  90                  95

Arg Ile Gly Arg Val Thr Gly Ser Asp Gly Lys Leu Tyr His Ile Tyr
                100                 105                 110

Val Glu Val Asp Gly Glu Ile Leu Leu Lys Gln Ala Lys Arg Gly Thr
                115                 120                 125

Pro Arg Thr Leu Lys Trp Thr Arg Asn Thr Thr Asn Cys Pro Leu Trp
130                 135                 140

Val Thr Ser Cys Gln Pro Asp Ala Ile Asn Ala Pro Val Thr Cys Cys
145                 150                 155                 160

Tyr Asn Phe Thr Asn Arg Lys Ile Ser Val Gln Arg Leu Ala Ser Tyr
                165                 170                 175

Arg Arg Ile Thr Ser Ser Lys Cys Pro Lys Glu Ala Val Ile Phe Lys
                180                 185                 190
```

```
Thr Ile Val Ala Lys Glu Ile Cys Ala Asp Pro Lys Gln Lys Trp Val
            195                 200                 205

Gln Asp Ser Met Asp His Leu Asp Lys Gln Thr Gln Thr Pro Lys Thr
210                 215                 220
```

<210> SEQ ID NO 6
<211> LENGTH: 164
<212> TYPE: PRT
<213> ORGANISM: CSFV

<400> SEQUENCE: 6

```
Met Glu Pro Leu Tyr Asp Lys Asn Gly Ala Val Leu Phe Gly Glu Pro
1               5                   10                  15

Ser Asp Thr His Pro Gln Ser Thr Leu Lys Leu Pro His Pro Arg Gly
            20                  25                  30

Glu Lys Glu Val Ile Val Gly Ile Arg Asp Leu Pro Arg Lys Gly Asp
        35                  40                  45

Cys Arg Thr Gly Asn Arg Leu Gly Pro Val Ser Gly Leu Phe Val Lys
50                  55                  60

Pro Gly Pro Val Phe Tyr Gln Asp Tyr Ser Gly Pro Val Tyr His Arg
65                  70                  75                  80

Ala Pro Leu Glu Gln Phe Lys Gln Ala Pro Met Cys Glu Val Thr Lys
                85                  90                  95

Arg Ile Gly Arg Val Thr Gly Ser Asp Gly Asn Leu Tyr His Met Tyr
            100                 105                 110

Val Cys Thr Asp Gly Cys Ile Leu Val Lys Thr Ala Lys Arg Glu Gly
        115                 120                 125

Gln Asp Val Leu Lys Trp Val Tyr Asn Val Leu Asp Ser Pro Ile Trp
130                 135                 140

Val Ala Ser Cys Ser Val Asp Lys Leu Ala Ala Leu Glu His His
145                 150                 155                 160

His His His His
```

<210> SEQ ID NO 7
<211> LENGTH: 156
<212> TYPE: PRT
<213> ORGANISM: CSFV

<400> SEQUENCE: 7

```
Met Glu Pro Val Tyr Asp Thr Ala Gly Arg Pro Leu Phe Gly Asn Pro
1               5                   10                  15

Ser Glu Val His Pro Gln Ser Thr Leu Lys Leu Pro His Asp Arg Gly
            20                  25                  30

Glu Asp Asp Ile Glu Thr Thr Leu Arg Asp Leu Pro Arg Lys Gly Asp
        35                  40                  45

Cys Arg Ile Tyr Ile Lys Pro Gly Pro Val Tyr Tyr Gln Asp Tyr Thr
50                  55                  60

Gly Pro Val Tyr His Arg Ala Pro Leu Glu Phe Phe Asp Glu Thr Gln
65                  70                  75                  80

Phe Glu Glu Thr Thr Lys Arg Ile Gly Arg Val Thr Gly Ser Asp Gly
                85                  90                  95

Lys Leu Tyr His Ile Tyr Val Glu Val Asp Gly Glu Ile Leu Leu Lys
            100                 105                 110

Gln Ala Lys Arg Gly Thr Pro Arg Thr Leu Lys Trp Thr Arg Asn Thr
        115                 120                 125

Thr Asn Cys Pro Leu Trp Val Thr Ser Cys Asp Thr Ser Val Asp Lys
```

130                 135                 140
Leu Ala Ala Ala Leu Glu His His His His His
145                 150                 155

<210> SEQ ID NO 8
<211> LENGTH: 332
<212> TYPE: PRT
<213> ORGANISM: CSFV

<400> SEQUENCE: 8

Met Glu Pro Leu Tyr Asp Lys Asn Gly Ala Val Leu Phe Gly Glu Pro
1               5                   10                  15

Ser Asp Thr His Pro Gln Ser Thr Leu Lys Leu Pro His Pro Arg Gly
                20                  25                  30

Glu Asp Glu Val Glu Val Gly Ile Arg Asp Leu Pro Arg Lys Gly Asp
            35                  40                  45

Cys Arg Thr Gly Asn Arg Leu Gly Pro Val Ser Gly Leu Phe Val Lys
        50                  55                  60

Pro Gly Pro Val Phe Tyr Gln Asp Tyr Ser Gly Pro Val Tyr His Arg
65                  70                  75                  80

Ala Pro Leu Glu Gln Phe Lys Gln Thr Pro Met Glu Glu Thr Thr Lys
                85                  90                  95

Arg Ile Gly Arg Val Thr Gly Ser Asp Gly Asn Leu Tyr His Met Tyr
            100                 105                 110

Val Glu Thr Asp Gly Glu Ile Leu Val Lys Gln Ala Lys Arg Glu Gly
        115                 120                 125

Gln Asp Val Leu Lys Trp Thr Tyr Asn Thr Leu Asp Ser Pro Ile Trp
130                 135                 140

Val Thr Ser Cys Ser Val Met Ala Thr Lys Ala Val Cys Val Leu Lys
145                 150                 155                 160

Gly Asp Gly Pro Val Gln Gly Ile Ile Asn Phe Glu Gln Lys Glu Ser
                165                 170                 175

Asn Gly Pro Val Lys Val Trp Gly Ser Ile Lys Gly Leu Thr Glu Gly
            180                 185                 190

Leu His Gly Phe His Val His Glu Phe Gly Asp Asn Thr Ala Gly Cys
        195                 200                 205

Thr Ser Ala Gly Pro His Phe Asn Pro Leu Ser Arg Lys His Gly Gly
    210                 215                 220

Pro Lys Asp Glu Glu Arg His Val Gly Asp Leu Gly Asn Val Thr Ala
225                 230                 235                 240

Asp Lys Asp Gly Val Ala Asp Val Ser Ile Glu Asp Ser Val Ile Ser
                245                 250                 255

Leu Ser Gly Asp His Cys Ile Ile Gly Arg Thr Leu Val Val His Glu
            260                 265                 270

Lys Ala Asp Asp Leu Gly Lys Gly Gly Asn Glu Glu Ser Thr Lys Thr
        275                 280                 285

Gly Asn Ala Gly Ser Arg Leu Ala Cys Gly Val Ile Gly Thr Ala Gln
    290                 295                 300

Val Asp Asp Tyr Lys Asp Asp Asp Lys Gly Gly Gly Ser Gly
305                 310                 315                 320

Gly Gly Gly Ser Trp Ser His Pro Gln Phe Glu Lys
                325                 330

<210> SEQ ID NO 9
<211> LENGTH: 332

```
<212> TYPE: PRT
<213> ORGANISM: CSFV

<400> SEQUENCE: 9

Met Glu Pro Val Tyr Asp Thr Ala Gly Arg Pro Leu Phe Gly Asn Pro
1               5                   10                  15

Ser Glu Val His Pro Gln Ser Thr Leu Lys Leu Pro His Asp Arg Gly
            20                  25                  30

Glu Asp Asp Ile Glu Thr Thr Leu Arg Asp Leu Pro Arg Lys Gly Asp
        35                  40                  45

Cys Arg Ser Gly Asn His Leu Gly Pro Val Ser Gly Ile Tyr Ile Lys
    50                  55                  60

Pro Gly Pro Val Tyr Tyr Gln Asp Tyr Thr Gly Pro Val Tyr His Arg
65                  70                  75                  80

Ala Pro Leu Glu Phe Phe Asp Glu Thr Gln Phe Glu Glu Thr Thr Lys
                85                  90                  95

Arg Ile Gly Arg Val Thr Gly Ser Asp Gly Lys Leu Tyr His Ile Tyr
            100                 105                 110

Val Glu Val Asp Gly Glu Ile Leu Leu Lys Gln Ala Lys Arg Gly Thr
        115                 120                 125

Pro Arg Thr Leu Lys Trp Thr Arg Asn Thr Thr Asn Cys Pro Leu Trp
130                 135                 140

Val Thr Ser Cys Asp Thr Met Ala Thr Lys Ala Val Cys Val Leu Lys
145                 150                 155                 160

Gly Asp Gly Pro Val Gln Gly Ile Ile Asn Phe Glu Gln Lys Glu Ser
                165                 170                 175

Asn Gly Pro Val Lys Val Trp Gly Ser Ile Lys Gly Leu Thr Glu Gly
            180                 185                 190

Leu His Gly Phe His Val His Glu Phe Gly Asp Asn Thr Ala Gly Cys
        195                 200                 205

Thr Ser Ala Gly Pro His Phe Asn Pro Leu Ser Arg Lys His Gly Gly
    210                 215                 220

Pro Lys Asp Glu Glu Arg His Val Gly Asp Leu Gly Asn Val Thr Ala
225                 230                 235                 240

Asp Lys Asp Gly Val Ala Asp Val Ser Ile Glu Asp Ser Val Ile Ser
                245                 250                 255

Leu Ser Gly Asp His Cys Ile Ile Gly Arg Thr Leu Val Val His Glu
            260                 265                 270

Lys Ala Asp Asp Leu Gly Lys Gly Gly Asn Glu Glu Ser Thr Lys Thr
        275                 280                 285

Gly Asn Ala Gly Ser Arg Leu Ala Cys Gly Val Ile Gly Thr Ala Gln
    290                 295                 300

Val Asp Asp Tyr Lys Asp Asp Asp Lys Gly Gly Gly Gly Ser Gly
305                 310                 315                 320

Gly Gly Gly Ser Trp Ser His Pro Gln Phe Glu Lys
                325                 330

<210> SEQ ID NO 10
<211> LENGTH: 76
<212> TYPE: PRT
<213> ORGANISM: CSFV

<400> SEQUENCE: 10

Gln Pro Asp Ala Ile Asn Ala Pro Val Thr Cys Cys Tyr Asn Phe Thr
1               5                   10                  15
```

```
Asn Arg Lys Ile Ser Val Gln Arg Leu Ala Ser Tyr Arg Arg Ile Thr
            20                  25                  30

Ser Ser Lys Cys Pro Lys Glu Ala Val Ile Phe Lys Thr Ile Val Ala
            35                  40                  45

Lys Glu Ile Cys Ala Asp Pro Lys Gln Lys Trp Val Gln Asp Ser Met
            50                  55                  60

Asp His Leu Asp Lys Gln Thr Gln Thr Pro Lys Thr
 65              70              75

<210> SEQ ID NO 11
<211> LENGTH: 16
<212> TYPE: PRT
<213> ORGANISM: CSFV

<400> SEQUENCE: 11

Ser Val Asp Lys Leu Ala Ala Leu Glu His His His His His His
 1               5                  10                  15

<210> SEQ ID NO 12
<211> LENGTH: 184
<212> TYPE: PRT
<213> ORGANISM: CSFV

<400> SEQUENCE: 12

Ser Val Met Ala Thr Lys Ala Val Cys Val Leu Lys Gly Asp Gly Pro
 1               5                  10                  15

Val Gln Gly Ile Ile Asn Phe Glu Gln Lys Glu Ser Asn Gly Pro Val
            20                  25                  30

Lys Val Trp Gly Ser Ile Lys Gly Leu Thr Glu Gly Leu His Gly Phe
            35                  40                  45

His Val His Glu Phe Gly Asp Asn Thr Ala Gly Cys Thr Ser Ala Gly
            50                  55                  60

Pro His Phe Asn Pro Leu Ser Arg Lys His Gly Gly Pro Lys Asp Glu
 65              70                  75                  80

Glu Arg His Val Gly Asp Leu Gly Asn Val Thr Ala Asp Lys Asp Gly
                 85                  90                  95

Val Ala Asp Val Ser Ile Glu Asp Ser Val Ile Ser Leu Ser Gly Asp
                100                 105                 110

His Cys Ile Ile Gly Arg Thr Leu Val Val His Glu Lys Ala Asp Asp
                115                 120                 125

Leu Gly Lys Gly Gly Asn Glu Glu Ser Thr Lys Thr Gly Asn Ala Gly
        130                 135                 140

Ser Arg Leu Ala Cys Gly Val Ile Gly Thr Ala Gln Val Asp Asp Tyr
145                 150                 155                 160

Lys Asp Asp Asp Asp Lys Gly Gly Gly Ser Gly Gly Gly Gly Ser
                165                 170                 175

Trp Ser His Pro Gln Phe Glu Lys
            180
```

METHOD FOR PRODUCING A RECOMBINANT PROTEIN OF INTEREST BY USING THE $N^{pro}$ TECHNOLOGY The present invention relates to a process for the recombinant production of a desired heterologous polypeptide of interest by using the autoprotease $N^{pro}$ of Pestivirus-technology.

E. coli is widely used for expression of therapeutic proteins in large amounts. For medical applications a homogeneous N-terminus is important, but incomplete removal of the N-formylmethionine by methionine aminopeptidases may lead to undesirable microheterogeneity. Moreover, gene fusion technology is often used for recombinant protein expression. Some commonly used fusion tags as for instance glutathione-S-transferase (GST), maltose binding protein (MBP) or thioredoxin mediate solubility whereas others as for instance poly-His, FLAG, strep II or calmodulin-binding peptide (CBP) serve as affinity tags for easier purification. Gene fusion technology requires the removal of the tag from the final protein product by enzymatic or chemical cleavage with varying cleavage efficiencies and specificities. Self-cleaving tags like inteins, Sortase A (SrtA), FrpC protein or Cystein protease domain (CPD) as well as $N^{pro}$ autoprotease provide a useful alternative for expression of proteins with pharmaceutical relevance. Self-cleaving fusion tags for recombinant protein production are disclosed in Li, Biotech. Let. 33 (2011): 869-881; streamlined protein expression and purification using cleavable self-aggregating tags are reported by Xing et al., Microb. Cell Fact. 10 (2011): 42.

Overexpression of heterologous proteins in E. coli frequently leads aggregation and deposition in dense, insoluble particles, also known as inclusion bodies. Advantages of the expression in inclusion bodies are the high purity of the desired product and the easy purification by centrifugation after cell disruption. However, crucial steps are resolving and refolding of the protein into its native structure. Solubilisation usually is carried out in high concentrations of chaotropic agents like urea or guanidinium hydrochloride to reach complete unfolding. Reducing agents such as 2-mercaptoethanol (β-ME), dithiothreitol (DTT) or 1-monothioglycerol (MTG) are added to reduce non-native inter- and intramolecular disulfide bonds and keep the cysteins in a reduced state. Autoproteolytic cleavage and subsequent release of the fusion partner are initiated upon refolding following a monomolecular reaction with a reaction rate being only dependent on chaotrope concentration (Ueberbacher et al., Process Biochem. 44 (2009), 1217-1224).

A bottleneck step is the renaturation of the proteins. Elimination of hydrophobic intermolecular interaction during the first steps of refolding is crucial for successful renaturation at high protein concentrations and to prevent aggregation (Vallejo et al., Microb. Cell Fact. 3 (2004), 11). Several renaturation techniques are known. Due to its simplicity refolding by dilution is preferred to pressure treatment or chromatographic techniques, especially in production scale. Protein concentration, as well as chaotrop concentration are diminished in a single step preventing aggregation by intermolecular interactions. However, large volumes and low protein concentration burden downstream processing steps. (Jungbauer et al., J. Biotech. 128 (2007), 587-596).

It is therefore an object of the present invention to provide an improvement in renaturation of inclusion bodies which must be renaturated, especially for autoproteolytic cleavage and preparation of recombinant proteins downstream of the process. Preferably, the invention should enable low volumes and high protein concentrations for obtaining the protein of interest and provide a method which is suitable to be established in industrial production scale, specifically for proteins used in medicine. In addition, separation of the renaturation step of the autoprotease from that of the protein of interest would also be beneficial and would enable highly specific renaturation conditions.

Therefore, the present invention provides a method for producing a recombinant protein of interest, characterised in by the following steps:

(a) providing a fusion protein comprising an $N^{pro}$ autoprotease moiety and a protein of interest moiety in inclusion bodies, (b) solubilising the inclusion bodies, (c) allowing the fusion protein to be cleaved by the $N^{pro}$ autoprotease moiety under chaotropic conditions, wherein the recombinant protein of interest is cleaved from the fusion protein and wherein the recombinant protein of interest is not yet renatured or simultaneously renatured, and (d) recovering the protein of interest, optionally including a renaturing step for the protein of interest.

The present invention is an improvement in the recombinant production of a desired heterologous polypeptide of interest by using the autoprotease $N^{pro}$ of Pestivirus-technology. This technology usually provides the recombinant expression of a fusion polypeptide which comprises an autoproteolytic moiety directly or indirectly derived from autoprotease $N^{pro}$ of Pestivirus and a heterologous polypeptide of interest in a host cell, often a prokaryotic host cell, such as E. coli. The heterologous polypeptide or protein of interest is covalently coupled via a peptide bond to the $N^{pro}$ molecule. The protein of interest is released from the fusion protein through hydrolysis of the peptide bond between the C-terminal Cys168 of Npro and position 169 of the fusion polypeptide which represents the authentic N-terminal amino acid of the protein of interest to be produced according to the present invention. The heterologous polypeptide of interest is produced in the host cell in form of cytoplasmic inclusion bodies (IB), which are then isolated and treated in such a way, that the desired heterologous polypeptide is cleaved from the fusion polypeptide by the $N^{pro}$ autoproteolytic activity.

Fusion polypeptides comprising the autoprotease Npro of Pestivirus are therefore specifically useful for producing heterologous recombinant polypeptides. $N^{pro}$ is an autoprotease with length of 168 amino acids and an apparent $M_r$ of about 20 kD in vivo. It is the first protein in the polyprotein of Pestiviruses and undergoes autoproteolytic cleavage from the following nucleocapsid protein C. This cleavage takes place after the last amino acid in the sequence of $N^{pro}$, Cys168. The autoprotease $N^{pro}$ activity of Pestivirus always cleaves off the fusion partner at this clearly determined site, releasing a polypeptide of interest with homogenous N-terminus. In addition, the autoproteolytic activity of $N^{pro}$ can be induced in vitro, by application of special buffers, so that the polypeptide of interest can be obtained by cleavage of fusion polypeptides that are expressed in IBs.

N-terminal autoprotease $N^{pro}$ from Classical Swine Fever Virus (CSFV) used in this technology serves as an attractive tool for expression of therapeutic proteins in large amounts especially in E. coli. Medical applications require an authentic N-terminus of the recombinant proteins, which can be achieved by self-cleavage of N-terminally fused $N^{pro}$ autoprotease. In addition, $N^{pro}$ fusion technology also allows the expression of small or toxic peptides, which would be degraded immediately after their synthesis by host cell proteases (Achmüller et al., Nat. Methods (2007), 1037-1043). As the expression of N$^{pro}$ fusion proteins in *E. coli* leads to the formation of insoluble aggregates, known as inclusion bodies, appropriate resolving and renaturation protocols are required to obtain biological active proteins.

As already mentioned, in most cases solubilisation is carried out in chaotropic agents such as urea or guanidinium chloride at high concentrations in combination with reducing agents to abolish false formed disulfide bonds. Due to its simplicity refolding by dilution is widely used to initiate renaturation. Hence, large amounts of buffer are added to provide conditions, which allow the formation of the correct biological active structure. Accordingly, according to the present invention, an autoprotease is applied that shows cleavage activity at high urea concentrations. This enables a significant lowering of the amount of buffer required after the solubilisation step and thus reduce costs. Additionally, if target protein and autoprotease require different renaturation conditions, the two steps can be separated, which adds another advantage to such preferred embodiments. An autoprotease active at high chaotropic conditions separates the renaturation step of the autoprotease from that of the target protein and thereby enables highly specific renaturation conditions. In fact, renaturing of the protein of interest can be separated from the cleaving step by the autoprotease which enables a better control for the recovery of the protein of interest. In this case, the protein of interest can then be brought into full activity at any later stage and at a different place. In the prior art, the restoration of the activity of the autoprotease moiety (which led to cleavage of the fusion protein) was always directly connected to the renaturation of the whole fusion protein, including the protein of interest moiety. This preferred embodiment of the present invention allows a separated refolding of the autoprotease and target protein.

Accordingly, in a preferred method the inclusion bodies were generated in a recombinant production system, preferably in a prokaryotic host cell, especially in *E. coli* host cells.

Preferred conditions in step (b) correspond to a urea concentration of more than 5 M, preferably more than 6 M, especially more than 7.5 M. "Correspond to" means that either urea is present in the amount indicated or that another chaotropic substance (such as butanol, ethanol, guanidinium chloride, lithium perchlorate, magnesium chloride, phenol, propanol, sodium dodecyl sulfate, thiourea, etc., or combinations of different chaotropes, e.g. a mixture of urea and guanidinium hydrochloride) is present in a concentration which leads to the same chaotropic effect (measured as increase of the entropy of the system. For example, preferred guanidinium hydrochloride concentrations are more than 2.5 M, preferably more than 3 M, especially more than 3.75 or even more than 4 M. Preferably, in step (b), solubilisation of inclusion bodies is performed by subjecting the inclusion bodies to denaturising conditions.

Preferred chaotropic conditions in step (c) correspond to a urea concentration of 1.4 to 5 M, preferably from 2 to 5 M, especially from 2 to 4 M. Preferred guanidinium hydrochloride concentrations in step (c) are from 0.7 to 2.5 M, preferably 1 to 2.5 M, especially 1 to 2 M. Again, also combinations of different chaotropes can be applied, e.g. a mixture of urea and guanidinium hydrochloride.

The terms "kosmotrope" (order-maker) and "chaotrope" (disorder-maker) originally denoted solutes that stabilized, or destabilized respectively, proteins and membranes. Later they referred to the apparently correlating property of increasing, or decreasing respectively, the structuring of water. Such properties may vary dependent on the circumstances, method of determination or the solvation shell(s) investigated. An alternative term used for kosmotrope is "compensatory solute" as they have been found to compensate for the deleterious effects of high salt contents (which destroy the natural hydrogen bonded network of water) in osmotically stressed cells. Both the extent and strength of hydrogen bonding may be changed independently by the solute but either of these may be, and has been, used as measures of order making. It is, however, the effects on the extent of quality hydrogen bonding that is of overriding importance. The ordering effects of kosmotropes may be confused by their diffusional rotation, which creates more extensive disorganized junction zones of greater disorder with the surrounding bulk water than less hydrated chaotropes. Most kosmotropes do not cause a large scale net structuring in water.

Ionic kosmotropes (or: "antichaotropes" to distinguish them from non-ionic kosmotropes) should be treated differently from non-ionic kosmotropes, due mainly to the directed and polarized arrangements of the surrounding water molecules. Generally, ionic behaviour parallels the Hofmeister series. Large singly charged ions, with low charge density (e.g. $SCN^-$, $H_2PO_4^-$, $HSO_4^-$, $HCO_3^-$, $I^-$, $Cl^-$, $NO_3^-$, $NH_4^+$, $Cs^+$, $K^+$, $(NH_2)_3C^+$ (guanidinium) and $(CH_3)_4N^+$ (tetramethylammonium) ions; exhibiting weaker interactions with water than water with itself and thus interfering little in the hydrogen bonding of the surrounding water), are chaotropes whereas small or multiply-charged ions, with high charge density, are kosmotropes (e.g. $SO_4^{2-}$, $HPO_4^{2-}$, $Mg^{2+}$, $Ca^{2+}$, $Li^+$, $Na^+$, $H^+$, $OH^-$ and $HPO_4^{2-}$, exhibiting stronger interactions with water molecules than water with itself and therefore capable of breaking water-water hydrogen bonds). The radii of singly charged chaotropic ions are greater than 1.06 Å for cations and greater than 1.78 Å for anions. Thus the hydrogen bonding between water molecules is more broken in the immediate vicinity of ionic kosmotropes than ionic chaotropes. Reinforcing this conclusion, a Raman spectroscopic study of the hydrogen-bonded structure of water around the halide ions $F^-$, $Cl^-$, $Br^-$ and $I^-$ indicates that the total extent of aqueous hydrogen bonding increases with increasing ionic size and an IR study in $HDO:D_2O$ showed slow hydrogen bond reorientation around these halide ions getting slower with respect to increasing size. It is not unreasonable that a solute may strengthen some of the hydrogen bonds surrounding it (structure making; e.g. kosmotropic cations will strengthen the hydrogen bonds donated by the inner shell water molecules) whilst at the same time breaking some other hydrogen bonds (structure breaker; e.g. kosmotropic cations will weaken the hydrogen bonds accepted by the inner shell water molecules). Other factors being equal, water molecules are held more strongly by molecules with a net charge than by molecules with no net charge; as shown by the difference between zwitterionic and cationic amino acids.

Weakly hydrated ions (chaotropes, $K^+$, $Rb^+$, $Cs^+$, $Br^-$, $I^-$, guanidinium$^+$) may be "pushed" onto weakly hydrated surfaces by strong water-water interactions with the transition from strong ionic hydration to weak ionic hydration occurring where the strength of the ion-water hydration approximately equals the strength of water-water interactions in bulk solution (with $Na^+$ being borderline on the strong side and $Cl^-$ being borderline on the weak side). Neutron diffraction studies on two important chaotropes (guanidinium and thiocyanate ions) show their very poor hydration, supporting the suggestion that they preferentially interact with the protein rather than the water. In contract to the kosmotropes, there is little significant difference between the properties of ionic and nonionic chaotropes due to the low charge density of the former.

Optimum stabilization of biological macromolecule by salt requires a mixture of a kosmotropic anion with a chaotropic cation.

Chaotropes break down the hydrogen-bonded network of water, so allowing macromolecules more structural freedom and encouraging protein extension and denaturation. Kosmotropes are stabilizing solutes which increase the order of water (such as polyhydric alcohols, trehalose, trimethylamine N-oxide, glycine betaine, ectoine, proline and various other zwitterions) whereas chaotropes create weaker hydrogen bonding, decreasing the order of water, increasing its surface tension and destabilizing macromolecular structures (such as guanidinium chloride and urea at high concentrations). Recent work has shown that urea weakens both hydrogen bonding and hydrophobic interactions but glucose acts as a kosmotrope, enhancing these properties. Thus, when urea molecules are less than optimally hydrated (about 6-8 moles water per mole urea) urea hydrogen bonds to itself and the protein (significantly involving the peptide links) in the absence of sufficient water, so becoming more hydrophobic and hence more able to interact with further sites on the protein, leading to localized dehydration-led denaturation. Guanidinium is a planar ion that may form weak hydrogen bonds around its edge but may establish strongly-held hydrogen-bonded ion pairs to protein carboxylates, similar to commonly found quaternary structural arginine-carboxylate "salt" links. Also, guanidinium possesses rather hydrophobic surfaces that may interact with similar protein surfaces to enable protein denaturation. Both denaturants may cause protein swelling and destructuring by sliding between hydrophobic sites and consequently dragging in hydrogen-bound water to complete the denaturation.

Generally the kosmotropic/chaotropic nature of a solute is determined from the physical bulk properties of water, often at necessarily high concentration. The change in the degree of structuring may be found, for example, using NMR or vibrational spectroscopy. Protein-stabilizing solutes (kosmotropes) increase the extent of hydrogen bonding (reducing the proton and $^{17}O$ spin-lattice relaxation times) whereas the NMR chemical shift may increase (showing weaker bonding e.g. the zwitterionic kosmotrope, trimethylamine N-oxide) or decrease (showing stronger bonding e.g. the polyhydroxy kosmotrope, trehalose). Trehalose shows both a reduction in chemical shift and relaxation time, as to a lesser extent does the protein stabilizer $(NH_4)_2SO_4$, whereas NaCl only shows a reduction in chemical shift and the protein destabilizer KSCN shows an increase in relaxation time and a reduction in chemical shift. Vibrational spectroscopy may make use of the near-IR wavelength near 5200 $cm^{-2}$ ($v_2+v_3$ combination), which shifts towards longer wavelength (smaller wavenumber) when hydrogen bonds are stronger.

One of the most important kosmotropes is the non-reducing sugar α,α-trehalose. It should perhaps be noted that trehalose has a much more static structure than the reducing sugars, due to its lack of mutarotation, or the other common non-reducing disaccharide, sucrose, due to its lack of a furan ring.

Accordingly, the term "chaotropic conditions" has to be regarded individually on the nature of the liquid starting preparation (which may e.g. be a solution, a suspension, an emulsion, a two- or three phase liquid system, etc.), especially—in preparations containing more than one phase—on the aqueous phase of the preparation. Preferred chaotropic conditions in step (c) in the method according to the present invention are those which correspond to a urea concentration of 1.4 to 5 M (especially in a buffered salt solution, such as 8.0 g NaCl, 0.2 g KCl, 1.44 g $Na_2HPO_4$, 0.24 g $KH_2PO_4$ ad 1000 ml with A. dest., pH 7.4 with HCl). Correspondence of chaotropic conditions (as well as reduction of chaotropicity ("lower" or "less" chaotropic conditions")) may be easily determined by the methods mentioned above as well as by applying the teachings of the Hofmeister series. Addition of various substances in the starting liquid have to be checked in individual cases in order to provide optimum binding/non-aggregating conditions for binding. For example, the use of reduction agents should be optimised to correspond to an amount of 0.05 to 50 mM dithiothreitole (DTT), especially 0.1 to 10 mM DTT. Furthermore, also the addition of detergents may, as described above, influence the chaotropicity of the starting preparation.

The term "denatured form" (or "non-refolded form") in the meaning of the present invention designates the biologically inactive form of the expressed fusion protein, as obtained as a product of the recombinant production process, usually as obtained after solubilising the inclusion bodies (under conditions under which the native three dimensional structure of the fusion protein is disrupted).

The term "refolding" (or "renaturing") refers to the mechanism during which the solubilized protein or part of protein (said part being associated to a specific activity of the part, if renatured) regains its native conformation and biological activity (or the biological activity of the part, respectively), i.e. reconstituting a protein from its denatured, inactive state to its active form (see also: Kaar et al., Biotech. Bioeng. 104 (2009), 774-784).

The term "autoproteolytic function", "autoproteolytic activity" or "autoproteolytic" refers to the autoproteolytic activity of one of the moieties of the fusion protein, which is inhibited while the fusion protein is in its denatured state and which is activated upon partial—(i.e. the autoprotease moiety) or complete refolding of the fusion protein. As used herein the term "autoprotease" shall refer to a polypeptide that possesses autoproteolytic activity and is capable of cleaving itself from a polypeptide moiety, i.e. the $N^{pro}$ autoprotease cleaves itself from the protein of interest part of the fusion protein according to the present invention.

As used herein, the term "recovering" shall refer to the obtaining of the protein of interest in purified form, i.e. by essentially separating the protein of interest from other proteins present in the expression/processing system, especially the autoprotease, but also all other proteins or other components which should not be present in the intermediate or final product. The protein of interest recovered by the method according to the present invention may be commercialised in the bulk form obtained directly from the cleaving step according to the present invention or further purified and/or formulated into a specific formulation, e.g. into a pharmaceutical formulation.

As used herein the term "inclusion bodies" shall refer to insoluble aggregates containing heterologous polypeptides (the fusion protein according to the present invention) present in the cytoplasm of transformed host cells. These appear as bright spots under the microscope and can be recovered by separation of the cytoplasm. The inclusion bodies are usually solubilised using a chaotropic agent. Upon solubilisation inclusion bodies are dissolved and a monomolecular suspension with substantially reduced intra- and inter-molecular interactions is aimed. Preferred solvents are urea, guanidine HCl and strong ionic detergents as N-lauroylsarcosine. In another embodiment of the present invention inclusion bodies are also solubilised using an aqueous alcohol solution at alkaline pH or simply an aqueous solution at alkaline pH.

As used herein the term "solubilisation" shall refer to the process necessary to dissolve the inclusion bodies. Solubilisation is aimed to result in a monomolecular dispersion of the polypeptides with minimum intra- and inter-molecular interactions. A preferred way of solubilisation of inclusion bodies within the scope of the present invention, is conducted by suspension in 50 mM Tris/HCl, 8 M urea, pH 7.3, adding a reducing agent, e.g. 50 mM DTT, in the case that oxidized cysteine residues are present. Where necessary it is possible to remove potentially insoluble material, for example by centrifugation. In the case that the inactive fusion protein is produced soluble within the cell, the clarified cell homogenate is subjected to the further work up described below for the solubilized inclusion bodies.

For the present invention, the refolding (renaturing) of the autoproteolytic activity in step (c) is performed under chaotropic conditions, i.e. under conditions wherein the protein of interest moiety is preferably still present in a non-refolded form. Refolding of the protein of interest can be achieved (after cleaving) by making the conditions less chaotropic, e.g. by dilution, addition of kosmotropic substances or elimination of chaotropic substances. On the other hand, the protein of interest may also be renatured simultaneously with the autoprotease moiety in step (c), i.e. under chaotropic conditions.

It is also preferred to carry out step (c) under chaotropic conditions which still allow a substantial cleavage rate so that the process can be conducted in appropriate reaction times, specifically in large scale set-ups. The autoproteolytic cleavage rate can be determined, for example, by initially solubilising the isolated/purified inclusion bodies in 7 M guanidine/HCl solution and then diluting 1:100 in reaction solution. After incubation for about 24 h, the reaction solution is examined by SDS-PAGE for cleavage having taken place. A Western blot is carried out to identify the proportions processed and unprocessed. The proportion of cleaved material can be determined by densitometric analysis of the Coomassie-stained SDS-PAGE gel. Higher chaotropic conditions would support the solubilisation process, however, usually decrease the cleavage rate of the autoprotease. A cleavage rate which is too low does not allow a proper industrial use of the present method, at least on a large-scale set-up. The N$^{pro}$ autoprotease moiety therefore has a preferred cleavage rate at 2.5 M urea of at least 20%, preferably at least 30%, especially at least 40%. If, for example incubation of the N$^{pro}$ autoprotease moiety of a specific fusion protein for 24 h at 2.5 M results in 50% of the amount of the material being cleaved (as determined by densitometric analysis of the Coomassie-stained SDS-PAGE gel), the N$^{pro}$ autoprotease moiety is defined to have a cleavage rate at 2.5 M urea of 50%.

Preferred N$^{pro}$ autoprotease moieties to be applied in the present method have a sequence selected from the group consisting of SEQ ID nos. 1 or 2 (Δ21N$^{pro}$ (HoBi) or N$^{pro}$ (HoBi)(UniProt Database accession no. Q5L4B1)).

In a preferred embodiment of the present invention, the N$^{pro}$ autoprotease moiety has a sequence wherein the interferon regulatory factor 3 binding site is deleted. This deletion provides that the final product is essentially free of impurities which might interfere with the interferon production of humans.

The present method can in principle be applied for production of any protein of interest, especially for all proteins known to be producible by the N$^{pro}$ autoprotease technique. Since the method according to the present invention is suitable for large-scale manufacturing and pharmaceutical good manufacturing practice, it is preferred to produce a protein for therapeutic use in humans with the present method, preferably a human recombinant protein or a vaccination antigen. Preferred proteins of interest therefore include the proteins referred to as the 151 recombinant pharmaceuticals approved for human use by the FDA or by the EMEA by 2009 in the review of Ferrer-Miralles et al. (Microbial Cell Factories 8 (2009), 17 doi:10.1186/1475-2859-8-17), especially the products based on proteins which have already been produced in an *E. coli* host cell: Dukoral (Oral cholera vaccine), Pegasys (Peginterferon alfa-2a), PegIntron (Peginterferon alfa-2b), Infergen (Interferon alfacon-1), Rebetron (Interferon alfa-2b), Roferon A (Interferon alfa-2$^a$), Viraferon (Interferon alfa-2b), ViraferonPeg (Peginterferon alfa-2b), Intron A (Interferon alfa-2b), Beromun (Tasonermin), Actimmune (Interferon gamma-1b), IPLEX (Mecasermin rinfabate recombinant), Kepivance (Palifermin), Neulasta (Pegfilgrastim), Neumega (Oprelvekin), Neupogen (Filgrastim), Humalog (Insulin lispro), Humatrope (Somatotropin), Humulin (Human insulin), Insuman (Human insulin), Lantus (Insulin glargine), Fortical (Salmon calcitpnin), Apidra (Insulin glulisine), Exubera (Human insulin), Forcaltonin (Salmon calcitonin), Forsteo (Teriparatide), Forsteo/Forteo (Teriparatide), Genotropin (Somatotropin), Glucagon, Increlex (Mecasermin), Insulin human Winthrop (Insulin human), Norditropin (Somatropin), Nutropin (Somatropin), NutropinAQ (Somatropin), Optisulin (Insulin glargine), Preotact (Human parathyroid hormone), Protropin (Somatrem), Somavert (Pegvisomant), Betaferon/Betaseron (Interferon beta-1b), Lucentis (Ranibizumab), Natrecor (Nesiritide), Rapilysin/Retavas e (Reteplase), Ontak (Denileukin diftitox), Kineret (Anakinra), and Omnitrope (Somatropin).

The process parameters can be optimised for each set-up, preferably depending on the N$^{pro}$ autoprotease used and on the protein of interest to be produced. For example, step (b) and/or step (c) can be performed at a pH of 5 to 11, preferably at a pH of 6 to 9.5, especially at a pH from 6.5 to 8.5. In a preferred embodiment, basic conditions are applied, especially in step (b), e.g. by the presence of more than 5 mM NaOH or KOH, preferably more than 25 mM NaOH or KOH, more preferred of more than 50 mM NaOH or KOH, especially more than 100 mM NaOH or KOH (or mixtures of KOH and NaOH); or other basic components (or mixtures thereof) resulting in a pH of more than 10, especially of a pH from 11 to 14. A specifically preferred embodiment of step (b) applies denaturing conditions to the fusion protein, preferably by a mixture of urea guanidinium hydrochloride and NaOH.

Preferably, step (b) and/or (c) is performed in a buffer, especially a phosphate, hydrogen phosphate or Tris/HCl buffer. The buffer may also comprise salts, such as NaCl, polyols, such as glycerol or carbohydrates, or detergents, such as non-ionic detergents, anionic detergents, cationic detergents, zwitterionic detergents, non-detergent sulfobetains, e.g. cetyl trimethylammonium chloride (CTAC), sodium dodecyl sulfate (SDS), lithium dodecyl sulfate (LDS) or N-lauroyl sarcosine.

It is also preferred to perform step (c) in the presence of a buffer comprising NaCl, preferably of 50 to 1000 mM NaCl, especially of 100 to 500 mM NaCl; phosphate ions and/or hydrogen phosphate ions, preferably 5 to 500 mM phosphate and/or hydrogen phosphate, especially 10 to 200 mM phosphate and/or hydrogen phosphate; glycerol, preferably 1 to 10% glycerol, especially 2 to 8% glycerol;

Tris/HCl, preferably 1 mM to 5 M Tris/HCl, especially 5 mM to 2 M Tris/HCl. The buffer used in step (c) can further contain one or more of the following ingredients: L-arginine, low concentrations of denaturants, detergents, cyclodextrins, polyethylene glycol, low-molecular weight non-detergent zwitterionic agents such as sulfobetaines, substituted pyridines and pyrroles, and acid substituted aminocyclohexanes.

According to a preferred embodiment, the renaturing step for the protein of interest is carried out after recovery of the protein of interest. For example, the renaturing step for the protein of interest can be carried out after full purification of the protein of interest. This embodiment is highly advantageous in those instances where the protein of interest is more stable in the non-renatured form than in the fully renatured ("active") form of this protein. Accordingly, the protein of interest can even be formulated into a pharmaceutical composition (e.g. a dry (lyophilised) composition) which may be reconstituted immediately before administration to a patient. In such a case, renaturing of the protein of interest is carried out by such reconstitution immediately before administration. This overcomes the risk that activity of the protein of interest is lost before (e.g. during purification after cleavage, formulation into a pharmaceutical product or storage of such a protein/pharmaceutical formulation).

The cleaving step (c) can be carried out in solution; however, according to a preferred embodiment, such cleaving (i.e. refolding of the autoprotease moiety to gain autoproteolytic activity) can be performed with the fusion protein being immobilised on a solid support. Refolding of the autoprotease (and enabling proteolytic activity) can then be initiated under chaotropic conditions according to the present invention whereafter the proteolytic activity is activated on the solid support. The cleaved part (either the C-terminal autoprotease (if the protein of interest is coupled to the solid support) or the protein of interest (if an autoprotease moiety is coupled to the solid support)) is then released from the solid support and can be easily recovered. Therefore, according to a preferred embodiment of the present method, the fusion protein is immobilised on a solid support and step (c) is carried out so that the autoproteolytic activity of $N^{pro}$ autoprotease is formed on the solid support.

As solid phase material, all materials already applied in the present field are appropriate. Preferably, the solid phase is selected from the group consisting of chromatography material, especially supports based on cellulose, agarose, acrylamide, poly(styrene-divinylbenzene) or ethylene glycol-methacrylate copolymers, microtiter plates, nitrocellulose membranes, microchips, glass plates, or metal coated supports.

According to the present invention various types of solid phase supports may be used, such as the supports based on cellulose, agarose (Sepharose or Macro-Prep gels), dextran (Sephadex gels), acrylamide (Sephacryl, Trisacryl gels), silica (TSK, SW gels), poly(styrene-divinylbenzene) (Source or Poros gels), ethylene glycol-methacrylate copolymers (Toyopearl HW, TSK, PW, fractogel EMD gels) or mixtures, in particular of agarose and dextran (Superdex gel). The supports approved for human or veterinary use by the competent American authorities (FDA for food and drug administration) or the European Union agencies will be more particularly selected. In addition, the support selected can be bonded, preferably by covalent bonding, to an affinity ligand (the support is said to be functionalized). The solid phase matrix may comprise, as the matrix backbone, any natural or synthetic and organic or inorganic material known per se to be applicable in solid phase separation of proteins and other biomolecules, e.g. natural or synthetic polysaccharides such as agar-agar and agaroses; celluloses, cellulose ethers such as hydroxypropyl cellulose, carboxymethyl celluose; starches; gums such as guar gum, and gum arabic, gum ghatti, gum tragacanth, locust bean gum, xanthan gum; pectins; mucins; dextrans; chitins; chitosans; alginates; carrageenans; heparins; gelatins; synthetic polymers such as polyamides such as polyacrylamides and polymethacrylamides; polyimides; polyesters; polyethers; polymeric vinyl compounds such as polyvinylalcohols and polystyrenes; polyalkenes; inorganic materials such as silicious materials such as silicon dioxide including amorphous silica and quartz; silicas; metal silicates, controlled pore glasses and ceramics; metal oxides and sulfides, or combinations of these natural or synthetic and organic or inorganic materials.

The matrix backbone is preferably selected from agar-agar, agaroses, celluloses, cellulose ethers such as hydroxypropyl cellulose, carboxymethyl cellulose, polyamides such as poly(meth)acryl-amides, polyvinylalcohols, silicas, and controlled pore glasses.

Especially interesting solid phase materials as matrix backbones are e.g. agar or agarose beads such as Sepharose and Superose beads from Pharmacia Biotech, Sweden and Biogel A from Biorad, USA; dextran based beads such as Sephadex, Pharmacia Biotech; cellulose based beads and membranes such as Perloza cellulose from Secheza, Czechoslovakia; composite beads such as Sephacryl and Superdex, Pharmacia Biotech; beads of synthetic organic polymers such as Fractogel from Toso-Haas, USA; POROS media from Perceptive Biosystems, USA, Bio-Rex, Bio-Gel P and Macro Prep from Biorad, HEMA and Separon from TESSEK and Hyper D and Trisacryl media from BioSepra, USA, Enzacryl and Azlactone, 3M, USA; beads of siliceous materials such as controlled pore glass, PROSEP, from Bioprocesing, England and Spherocil, BioSepra; and coated silica composites in the form of beads or membranes such as ACTI-DISK, ACTI-MOD and CycloSep from Arbor Technologies, USA.

Typically, the solid phase matrix backbone, as well as the resulting functionalised solid phase matrix, may, e.g., be in the form of irregular particles or spherical beads, membranes or sheets, moulded surfaces, or sticks. The solid phase material may further be fully or partly permeable or completely impermeable to proteins. In a particularly interesting embodiment of the present invention, the matrix is in the form of irregular or spherical beads with sizes in the range of 1-10000 µm, preferably 10-1000 µm; such as 10-60 µm for high performance applications and such as 50-500 µm, preferably 50-300 µm, for preparative purposes. Preferred materials (polymethacrylate monoliths) for use in the present invention are disclosed in Junbauer et al. (J. Chromatogr. A 1184 (2008), 62-79).

A particular interesting form of matrix is a density controlled matrix in the form of a conglomerate comprising density controlling particles. These conglomerates are especially applicable in large scale operations for fluidised or expanded bed chromatography as well as different batch-wise chromatography techniques in non-packed columns, e.g. simple batch adsorption in stirred tanks.

Affinity ligands for the fusion protein according to the present invention may be attached to the solid phase material by any type of covalent bond known per se to be applicable for this purpose, either by a direct chemical reaction between the affinity ligand and the solid phase material or by a preceding activation of the solid phase material or of the ligand with a suitable reagent known per se making it possible to link the matrix backbone and the ligand. Examples of such suitable activating reagents are epichlorohydrin, epibromohydrin, allyl-glycidylether; bis-epoxides such as butanedioldiglycidylether; halogen-substituted aliphatic compounds such as di-chloro-propanol, divinyl sulfone; carbonyldiimidazole; aldehydes such as glutaric dialdehyde; quinones; cyanogen bromide; periodates such as sodium-meta-periodate; carbodiimides; chloro-triazines such as cyanuric chloride; sulfonyl chlorides such as tosyl chlorides and tresyl chlorides; N-hydroxy succinimides; 2-fluoro-1-methylpyridinium toluene-4-sulfonates; oxazolones; maleimides; pyridyl disulfides; and hydrazides. Among these, the activating reagents leaving a spacer group SP1 different from a single bond, e.g. epichlorohydrin, epibromohydrin, allyl-glycidylether; bis-epoxides; halogen-substituted aliphatic compounds; divinyl sulfone; aldehydes; quinones; cyanogen bromide; chloro-triazines; oxazolones; maleimides; pyridyl disulfides; and hydrazides, are preferred.

Especially interesting activating reagents are believed to be epoxy-compounds such as epichlorohydrin, allyl-glycidylether and butanedioldiglycidylether.

For peptide affinity chromatography within the scope of the present invention, any matrix useful for the immobilization of peptide ligands can be used. Preferably Fractogel epoxy (M), from Merck, Darmstadt, Germany) or equally preferred "monolithic chromatography medium" CIM-ep-oxy is used. The ligands can be immobilized either directly onto the chemically activated backbone of the chromatography matrix, or via a spacer or linker. In the latter case a spacer is coupled to the chromatographic matrix, said spacer is then chemically activated, in order to allow binding of the ligand. Preferably Fractogel epoxy matrices are used in combination with spacers.

In a particularly preferred embodiment of the present invention the spacer is generated by reaction of the chromatographic matrix with diaminodipropylamine (DADPA) and subsequent reaction with succinic anhydride (SA). The resulting terminal carboxy group on the spacer is chemically activated and preferably linked to a terminal amino-group. The ligand is immobilized on the matrix or on the spacer via a reactive group that it comprises. In the case of peptide ligands such reactive groups may be either the amino, carboxy or the sulfhydryl group. Within the present invention anchorage of the peptide on the matrix or the spacer via an amino bond is particularly preferred.

Preferably, the solid phase used according to the present invention is provided as affinity chromatography material, and exhibits oligopeptide ligands as disclosed in WO 2006/113958 A2.

Preferably the solid support is a chromatography column. In principle any chromatography material capable of selectively binding the fusion polypeptide (comprising $N^{pro}$ and the protein of interest) can be used within the framework of the present invention. The matrix of the chromatography may, in a preferred embodiment, be in the form of a column, however, it may also be in other forms, like beads or organic materials like polyethylene glycol modified with an affinity peptide.

Chromatography materials suitable for use within the present invention may be based on a cellulose binding domain, they may be cation exchange chromatography materials using polycationic tags like e.g. polyarginine or polylysine as well as anion exchange chromatography with polyanionic tags like e.g. polyasparagine. Accordingly within the present invention the use of an affinity chromatography material as solid support is preferably selected from the group consisting of immobilized metal ion chromatography (IMAC), cation exchange chromatography, anion exchange chromatography, cellulose binding domain chromatography and peptide affinity chromatography.

More preferably the affinity chromatography used is cation exchange chromatography, wherein the fusion polypeptide comprises a polycationic tag. Even more preferred is the use of either a polyarginine or polylysine affinity tag.

For cation exchange chromatography the expressed polypeptides preferably comprise an N-terminal polycationic tag, for example a polyarginine or polylysine tag. The solution containing the expressed polypeptide that was extracted from the host cells is (filtered) and loaded onto a column packed with any medium suitable for cation exchange chromatography such as e.g. SP Sepharose FF, CM Sepharose FF, Fractogel EMD SO3-. Preferably buffers with low conductivity are applied. After loading unbound material may be washed out and refolding may be started by Another preferred embodiment of the present invention is one, wherein the solid support is an affinity chromatography or an anion exchange chromatography and wherein the polypeptide to be bound to the column comprises a polyanionic tag. More preferably, polyasparagine is used as affinity tag.

A further preferred embodiment to achieve the desired binding properties is immobilized metal ion affinity chromatography (IMAC). Accordingly, in a preferred embodiment of the present invention the solid support is immobilized metal ion affinity chromatography (IMAC) material, and the polypeptide to be bound (especially the fusion protein comprising the second part of Npro and the protein of interest) comprises a metal chelate affinity tag. In this case the polypeptide is detected and bound by means of a metal chelate affinity tag comprised in it. In a more preferred embodiment of the present invention, the metal chelate affinity tag is a polyhistidine affinity tag. IMAC is based on the specific coordinate covalent binding between histidine or other suitable unique amino acids (either naturally present on the surface of the protein or grafted with recombinant DNA techniques) and various immobilized metal ions, such as copper, nickel, zinc, or iron. Chromatographic materials known in the art for the use in IMAC may also be useful within the present invention. In a preferred embodiment of the present invention, $Ni^{2+}$-Chelating Sepharose Fast flow (GE Healthcare, Uppsala, SE) is used as matrix.

Alternatively, the solid support may be an immunoaffinity chromatography material, employing epitope tags as described above which are present at the N-terminus of the polypeptide and are bound to the chromatographic matrix via an antibody recognizing said tag. Another preferred affinity chromatographic material is affinity chromatography using oligopeptide ligands as disclosed in WO 2006/113958 A.

A preferred embodiment of the present invention is characterized in that the fusion protein comprises additional moieties, preferably an affinity tag or a refolding aid moiety, especially a His-tag, SlyD (or parts of SlyD), oligo amino-acid stretches composed of either positive or negative charged moieties, Strep-tag and/or FLAG-tag.

According to a preferred embodiment, the fusion protein is purified or partially purified, especially between step (b) and step (c). Preferably, the fusion protein is purified or partially purified (especially between step (b) and step (c)) by affinity purification, preferably by affinity chromatography or affinity precipitation.

The present invention is carried out with the $N^{pro}$ technology. This technology is disclosed e.g. in WO 01/11057 A, WO 01/11056 A, WO 2006/113957 A, WO 2006/113958 A, WO 2006/113959 A, Cheng et al., Amino Acids 39 (5)

(2010): 1545-1552; Dürauer et al., Sep. Sci. Technol. 45 (2010): 2194-2209; Schmoeger et al., J. Chromatog. 1217 (2010): 5950-5956; Hahn et al., J. Chromatog. 1217 (2010): 6203-6213; and Achmüller et al., Nat. Meth. 4 (2007), 1037-1043. In general terms, the N$^{pro}$ technology relates to a process for the recombinant production of a heterologous protein of interest, comprising (i) cultivation of a bacterial host cell which is transformed with an expression vector which comprises a nucleic acid molecule which codes for a fusion protein, the fusion protein comprising a first polypeptide which exhibits the autoproteolytic function of an autoprotease N$^{pro}$ of a pestivirus, and a second polypeptide which is connected to the first polypeptide at the C-terminus of the first polypeptide in a manner such that the second polypeptide is capable of being cleaved from the fusion protein by the autoproteolytic activity of the first polypeptide, and the second polypeptide being a heterologous protein of interest, wherein cultivation occurs under conditions which cause expression of the fusion protein and formation of corresponding cytoplasmic inclusion bodies, (ii) isolation of the inclusion bodies from the host cell, (iii) solubilisation of the isolated inclusion bodies, (iv) dilution of the solubilisate to give a reaction solution in which the autoproteolytic cleavage of the heterologous protein of interest from the fusion protein is performed, and (v) isolation of the cleaved heterologous protein of interest ("recovering").

This technology is suited for a large variety of proteins of interest. For the purpose of the present invention, the terms "heterologous protein", "target protein", "polypeptide of interest" or "protein of interest" (and the like) mean a polypeptide which is not naturally cleaved by an autoprotease N$^{pro}$ of a Pestivirus from a naturally occurring fusion protein or polyprotein (i.e. a polypeptide being different than the naturally following amino acids 169ff of the Pestivirus polyprotein encoding the structural Protein C and subsequent viral proteins). Examples of such heterologous proteins of interest are industrial enzymes (process enzymes) or polypeptides with pharmaceutical, in particular human pharmaceutical, activity.

Due to its autocatalytic cleavage it enables synthesis of proteins with an authentic N-terminus which is especially important for pharmaceutical applications. Furthermore, not only large proteins ("proteins of interest") but also small peptides can be stably expressed by C-terminal linking to N$^{pro}$. A high expression rate forces the fusion protein into inclusion bodies. After purification, N$^{pro}$ is refolded and cleaves itself off.

It is essential that the protein of interest to be produced by the present invention is attached C-terminally after Cys168 of the N$^{pro}$ autoprotease, because this is the cleavage site where the peptidic bond between the C-terminus of the N$^{pro}$ moiety (at Cys168) and the protein of interest is cleaved in step (c) according to the present invention.

Examples of preferred proteins of interest with human pharmaceutical activity are cytokines such as interleukins, for example IL-6, interferons such as leukocyte interferons, for example interferon a2B, growth factors, in particular haemopoietic or wound-healing growth factors, such as G-CSF, erythropoietin, or IGF, hormones such as human growth hormone (hGH), antibodies or vaccines. Also very short polypeptides having only 5 to 30 amino acid residues can be produced as protein of interest by the present technology. The N$^{pro}$ technology has specific advantages in an expression system making use of inclusion bodies, because the strong aggregation bias of the fused autoprotease facilitates the formation of inert inclusion bodies, almost independent of the fusion partner. Accordingly, almost any protein of interest is producible with the present system in high amounts and yields. Reports are e.g. available for expression of synthetic interferon-a1; toxic gyrase inhibitor CcdB, a short 16-residue model peptide termed pep6His (SVDKLAAALEHHHHHH (SEQ ID No. 3)), human proinsulin, synthetic double domain D of staphylococcal protein A (sSpA-D$_2$), keratin-associated protein 10-4 (KRTAP10-4), synthetic green fluorescent protein variant (sGFPmut3.1), synthetic inhibitorial peptide of senescence evasion factor with N-terminal cysteine (C-sSNEVi), synthetic inhibitorial peptide of senescence evasion factor with randomized amino acid sequence with C-terminal cysteine (sSNEVscr-C); recombinant human monocyte chemoattractant protein 1 (rhMCP-1). So far, the only limitations with respect to high yields have been suspected for chaperones and proteins with comparable properties of supporting protein folding. Such proteins as fusion partners could suppress the aggregation bias of an N$^{pro}$ molecule, leading to lower yields due to less aggregation. Nevertheless, the present technology can even be applied for expressing such proteins counter-acting aggregation.

The fusion protein according to the present invention can additionally contain auxiliary sequences, such as affinity tags or refolding aid moieties; it may also contain more than one protein of interest (it can e.g. contain two or three or four or even more proteins of interest which may be separated from each other at a later stage or even at the same stage as the cleavage by the Npro autoprotease).

According to another aspect, the present invention also relates to an N$^{pro}$ autoprotease moiety (in isolated form or in form of a fusion polypeptide together with a protein of interest) that has improved chaotropic properties compared to wild type Npro or other known Npro variants, such as the EDDIE variants according to WO 2006/113957 A. The Npro moieties provided with the present invention have an unusual high propensity for beta aggregation. This has been found in the "HoBi" form (UniProt Database accession no. Q5L4B1). This high propensity for beta aggregation correlates with the specific properties of these autoproteases, namely high productivity and renaturation at high chaotropic conditions. With the present invention hydrophobic patches in naturally occurring N$^{pro}$ variants that are compatible with enzymatic activity are provided. Combining such hydrophobic patches on the original HoBi scaffold provided novel active N$^{pro}$ variants with improved properties concerning beta-aggregation during expression, inclusion bodies formation and renaturation. These Npro variants are therefore specifically suited for recombinant expression. Following amino acid exchanges in the HoBi protein sequence (SEQ. ID.No.2), alone or in combinations thereof, are provided in the novel molecules according to the present invention:
N28 to V, L or I; A30 to T; T39 to V or I; L81 to V, F82 to Y, V83 to I, K84 to E, P85 to L, P87 to A, V88 to I, Q91 to K; S94 to I, L or V; Q105 to L; P110 to V; N127 to K, M131 to I, T135 to V, V141 to L. In preferred embodiments of the Npro variants according to the present invention, at least two of such exchanges are present, more preferred, at least three exchanges, especially at least four exchanges.

These amino acid exchanges significantly affect the beta-aggregation propensity of the optimized HoBi-Npro and all these exchanges were tolerated during the evolution of the Pesti-virus species, as these exchanges have been found in enzymatically active Npro-variants.

Therefore, the present invention provides an N$^{pro}$ autoprotease moiety having a sequence comprising at least one amino acid exchange compared to SEQ ID No. 2, wherein the amino acid exchange is selected from the group consisting of N28 to V, L or I; A30 to T; T39 to V or I; L81 to V, F82 to Y, V83 to I, K84 to E, P85 to L, P87 to A, V88 to I, Q91 to K; S94 to I, L or V; Q105 to L; P110 to V; N127 to K, M131 to I, T135 to V, V141 to L.

The N$^{pro}$ autoprotease moiety according to the present invention may comprise at least two, preferably at least three, especially at least four amino acid exchanges selected from the group consisting of N28 to V, L or I; A30 to T; T39 to V or I; L81 to V, F82 to Y, V83 to I, K84 to E, P85 to L, P87 to A, V88 to I, Q91 to K; S94 to I, L or V; Q105 to L; P110 to V; N127 to K, M131 to I, T135 to V, V141 to L.

Preferably, amino acids 2 to 21 of SEQ ID No. 2 are deleted. This allows even more improved results in protein expression systems.

Another preferred exchange in the N$^{pro}$ autoprotease moieties according to the present invention is the exchange of A166 of SEQ ID No. 2 with T.

The present N$^{pro}$ autoprotease moieties (including the N$^{pro}$ autoprotease moiety according to SEQ ID No. 2) are specifically useful for the recombinant expression of proteins.

The present invention also relates to fusion proteins comprising a recombinant protein of interest and an N$^{pro}$ autoprotease moiety according to the present invention (including the N$^{pro}$ autoprotease moiety according to SEQ ID No. 2). The present invention also relates to nucleic acid molecules comprising a sequence encoding such N$^{pro}$ autoprotease moieties or fusion proteins, especially expression vectors for recombinant expression (with e.g. suitable promoters, marker genes (resistance markers, etc), etc.).

In line with the above teaching, the present invention specifically provides an N$^{pro}$ autoprotease moiety having a sequence selected from the group consisting of SEQ ID nos. 1 or (Δ21N$^{pro}$ (HoBi) or Npro(HoBi)). On the other hand, also known Npro autoprotease sequences can be applied, such as the N-terminal protease of Pestivirus strain D32/00_HoBi (GenBank Accession No. AAS68353.1).

According to a preferred embodiment, the present invention relates to the production of recombinant proteins with an exactly defined N-terminus (meaning a protein product in which all molecules have the same N-terminus; standard protein production in E. coli leads partly to proteins with N-formyl groups at the N-terminus, as well as proteins which lack the N-terminal methionine) using a variant of the pestiviral N$^{pro}$ autoprotease D32/00_"HoBi" (SEQ. ID.No.1), having i.a. a "TSC" motif at the C-terminus instead of the naturally occurring "ASC" motif (SEQ. ID.No.2; also referred to as "N$^{pro}$ (HoBi)") which shows autoproteolytic activity at high chaotropic conditions allowing specifically efficient separated refolding of autoprotease and target protein.

The present invention also relates to an expression vector encoding for a fusion protein comprising an N$^{pro}$ autoprotease according to SEQ:ID:NOs 1 and 2. In the expression vector to be employed in the process according to the present invention, the fusion polypeptide is operably linked to at least one expression control sequence. Expression control sequences are, in particular, promoters (such as the lac, tac, T3, T7, trp, gac, vhb, lambda pL or phoA promoter), ribosome binding sites (for example natural ribosome binding sites which belong to the abovementioned promoters, cro or synthetic ribosome binding sites), or transcription terminators (for example rrnB T1T2 or bla).

The vector may also contain sequences encoding fusion domains, as described below, that are present at the N-terminal end of the fusion polypeptide and that are required for its binding to the affinity chromatography system, e.g. polyamino acids like polylysine or, for immunoaffinity chromatography, so-called "epitope tags", which are usually short peptide sequences for which a specific antibody is available. Well known epitope tags for which specific monoclonal antibodies are readily available include FLAG, influenza virus haemagglutinin (HA), and c-myc tags.

In a preferred embodiment of the present invention, the expression vector is a plasmid.

Another aspect of the present invention relates to a host cell, preferably a prokaryotic host cell, especially an E. coli host cell, containing an expression vector according to the present invention. The transformed bacterial host cell, i.e. the expression strain, is cultivated in accordance with microbiological practice known per se. The host strain is generally brought up starting from a single colony on a nutrient medium, but it is also possible to employ cryo-preserved cell suspensions (cell banks). The strain is generally cultivated in a multistage process in order to obtain sufficient biomass for further use.

On a small scale, this can take place in shaken flasks, it being possible in most cases to employ a complex medium (for example LB broth). However, it is also possible to use defined media (for example citrate medium). Since in the preferred embodiment of the present invention it is intended that the expressed fusion polypeptide is in the form of insoluble inclusion bodies, the culture will in these cases be carried out at relatively high temperature (for example 30° C. or 37° C.). Inducible systems are particularly suitable for producing inclusion bodies (for example with the trp, lac, tac or phoA promoter).

On a larger scale, the multistage system consists of a plurality of bioreactors (fermenters), it being preferred to employ defined nutrient media. In addition, it is possible greatly to increase biomass and product formation by metering in particular nutrients (fed batch). Otherwise, the process is analogous to the shaken flask. In the process according to the present invention, the inclusion bodies are isolated from the host cell in a manner known per se. For example, after the fermentation has taken place, the host cells are harvested by centrifugation, micro filtration, flocculation or a combination thereof, preferably by centrifugation. The wet cell mass is disintegrated by mechanical, chemical or physical means such as high pressure homogenizer, beads mills, French press, Hughes press, osmotic shock, detergents, enzymatic lysis or a combination thereof. Preferably, disruption of the cells takes place by high pressure homogenization. In the preferred embodiment where the recombinant fusion polypeptide is deposited as inclusion bodies, the inclusion bodies can be obtained for example by means of high-pressure dispersion or, preferably, by a simple centrifugation at low rotor speed. The inclusion bodies are separated by centrifugation or microfiltration or a combination thereof. The purity in relation to the desired polypeptide of interest can then be improved by multiple resuspension of the inclusion bodies in various buffers, for example in the presence of NaCl (for example 0.5 1.0 M) and/or detergent (for example Triton X 100). Preferably the purity of the inclusion body preparation is improved by several washing steps with various buffers (e.g. 0.5% Deoxycholate followed by two times 1 M NaCl solution and finally distilled water). This usually results in removal of most of the foreign polypeptides from the inclusion bodies.

BRIEF DESCRIPTION OF THE DRAWINGS

The patent or application file contains at least one color drawing. Copies of this patent or patent application publication with color drawing will be provided by the USPTO upon request and payment of the necessary fee.

The present invention is further described by the following examples and the drawing figures, yet without being restricted thereto.

Left y-axis stands for the titer in [g/L]
Right y-axis stands for the specific titer in [mg/g DCW]
EDDIE stands for D21EDDIE-MCP-1 (SEQ.ID.NO. 5)
HoBi stands for D21N$^{pro}$ (HoBi)-MCP-1 (SEQ.ID.NO. 4)
a: titers of the fusion proteins
b: titers of MCP-1 within the fusion proteins
c: specific titer of MCP-1

Figure 11:
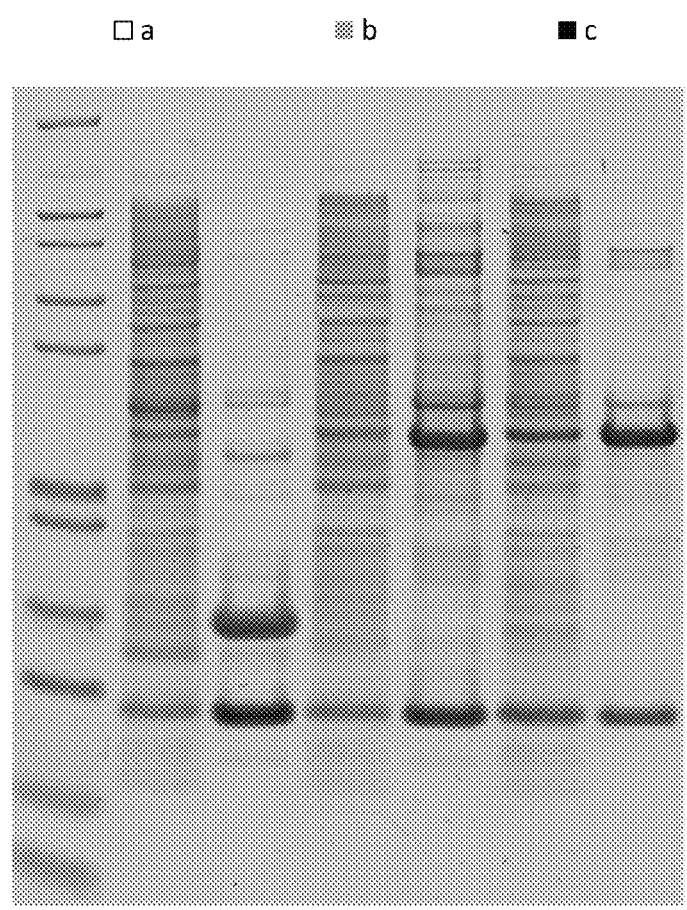

FIG. 11: Expression of N$^{pro}$-fusion proteins D21Npro (HoBi)-pep6His (SEQ.ID.NO. 6), D21Npro (HoBi)-SOD-FLS (SEQ.ID.NO. 8), D21EDDIE-pep6His (SEQ.ID.NO. 7) and D21EDDIE-SOD-FLS (SEQ.ID.NO. 9): SDS-PAGE of soluble (S) and insoluble (IB) fractions three hours after induction (20 μmol IPTG/g CDM).

Lane 1: molecular weight marker
Lane 2: D21Npro (HoBi)-pep6His (SEQ.ID.NO. 6), S
Lane 3: D21Npro (HoBi)-pep6His (SEQ.ID.NO. 6), IB
Lane 4: D21Npro (HoBi)-SOD-FLS (SEQ.ID.NO. 8), S
Lane 5: D21Npro (HoBi)-SOD-FLS (SEQ.ID.NO. 8), IB
Lane 6: D21EDDIE-SOD-FLS (SEQ.ID.NO. 9), S
Lane 7: D21EDDIE-SOD-FLS (SEQ.ID.NO. 9), IB FIG. 12: Refolding and Cleavage kinetic for D21Npro (HoBi)-SOD-FLS (SEQ.ID.NO. 8)(A) and D21EDDIE-SOD-FLS (SEQ.ID.NO. 9)(B) after solubilization in 8 M Urea and refolding in Tris buffer at a protein concentration of c=0.1 mg/L in presence of increasing concentration of residual Urea.

x-axis stands for time in [min]
y-axis stands for cleavage yield in [%]
A: cleavage yield in [%] at 0.4 M Urea
B: cleavage yield in [%] at 1 M Urea
C: cleavage yield in [%] at 2 M Urea
D: cleavage yield in [%] at 3 M Urea

EXAMPLES

Materials and Methods

Protein Expression

Δ21N$^{pro}$ (HOBi (SEQ.ID.No.1); deletion of amino acids 2 to 21 of (SEQ.ID.No.2)) was cloned into pET30a vectors harboring pep6His as well as SDD-diUbi-pep6His as target proteins using NdeI and SpeI. The vectors were transformed into E. coli BL21 (DE3) by electroporation and cells were grown over night at 37° C. Cells were diluted 1:100 and incubated at 37° C. until OD$_{600}$ reached 0.5. Protein expression was induced by addition of 1M IPTG (isopropyl β-D-1-thiogalactopyranoside) to a final concentration of 1 mM IPTG followed by an incubation for four hours at 37° C. Cells were harvested by centrifugation. Lysis was carried out using a french press. Inclusion bodies were harvested by a further centrifugation step.

```
Δ21 N^Pro (HoBi) autoprotease moiety
                                         (SEQ.ID.NO. 1)
MEPLYDKNGA VLFGEPSDTH PQSTLKLPHP RGEKEVIVGI

RDLPRKGDCR TGNRLGPVSG LFVKPGPVFY QDYSGPVYHR

APLEQFKQAP MCEVTKRIGR VTGSDGNLYH MYVCTDGCIL

VKTAKREGQD VLKWVYNVLD SPIWVTSC
```

The SVDKLAAALEHHHHHH motif (SEQ.ID.No.3) is a model peptide attached to the autoprotease moiety.

```
N^Pro (HoBi) autoprotease moiety
                                         (SEQ.ID.NO. 2)
MELLNFELLY KTYKQKPAGV QEPLYDKNGA VLFGEPSDTH

PQSTLKLPHP RGEKEVIVGI RDLPRKGDCR TGNRLGPVSG

LFVKPGPVFY QDYSGPVYHR APLEQFKQAP MCEVTKRIGR

VTGSDGNLYH MYVCTDGCIL VKTAKREGQD VLKWVYNVLD

SPIWVASC
```

Refolding in Different Buffers in Presence of 2.5M Urea

Inclusion bodies were solubilized in 8M Urea/50 mM $(NH_4)_2HPO_4$ pH 7.5/10 mM MTG and refolded in
a) buffer 1: 500 mM NaCl, 20 mM $(NH_4)_2HPO_4$ pH 7.5, 5% glycerol
b) buffer 2: 1M Tris/HCl pH 7.5, 5% glycerol
c) buffer 13: 300 mM Arg/HCl, 500 mM NaCl, 20 mM $(NH_4)_2HPO_4$ pH 9.0, 5% glycerol
d) buffer 17: 100 mM NaCl, 100 mM $(NH_4)_2HPO_4$ pH 7.5, 5% glycerol
e) buffer 19: 150 mM NaCl, 50 mM NaPhosphate pH 7.5, 5% glycerol
d) buffer 23: 150 mM NaCl, 20 mM Tris/HCl pH 7.5, 5% glycerol 8M Urea/50 mM $(NH_4)_2HPO_4$ pH7.5 was added to a final concentration of 2.5M. Refolding was stopped after 68 hours at 20° C. by centrifugation at 20,000×g. The supernatant was precipitated by TCA. Pellet and supernatant were re-suspended in a gel loading buffer containing 8M urea to prevent further refolding in sample buffer and analyzed by gel electrophoresis using Bis-Tris gels. After staining and destaining, gels were photographed and band intensities were determined by densitometry using an AlphaDigDoc 1200 instrument.

Refolding in 500 mM NaCl, 20 mM $(NH_4)_2HPO_4$ pH 7.5, 5% Glycerol Under Various Urea Concentrations Inclusion bodies were solubilized in 8M Urea/50 mM $(NH_4)_2HPO_4$ pH7.5/10 mM MTG (Methylthioglycerole) and refolded in 500 mM NaCl, 20 mM $(NH_4)_2HPO_4$ pH 7.5, 5% glycerol. 8M Urea/500 mM NaCl, 20 mM $(NH_4)_2HPO_4$ pH 7.5, 5% glycerol was added to the refolding batch to final concentrations of 2.5, 3, 3.5, 4 and 4.5 M Urea. Refolding was stopped after 44 h at 20° C. by centrifugation at 20,000×g for 15 minutes and room temperature and were resuspended in a gel loading buffer containing 8M urea to prevent further refolding in sample buffer and analyzed by gel electrophoresis using Bis-Tris gels. After staining and destaining, gels were photographed and band intensities were determined by densitometry using an AlphaDigDoc 1200 instrument.

Determination of the Refolding Kinetics in 500 mM NaCl, 20 mM $(NH_4)_2HPO_4$ pH 7.5, 5% Glycerol Under Three Different Urea Concentrations Inclusion bodies were solubilized in 8M Urea/500 mM NaCl, 20 mM $(NH_4)_2HPO_4$ pH7.5, 5% glycerol/10 mM MTG and refolded in 500 mM NaCl, 20 mM $(NH_4)_2HPO_4$ pH 7.5, 5% glycerol at 20° C. 8M Urea/500 mM NaCl, 20 mM $(NH_4)_2HPO_4$ pH 7.5, 5% glycerol was added to the refolding batch to final concentrations of 3, 3.5 and 4 M Urea. After defined time points (0.5, 1, 1.5, 2, 3, 4, 5, 6, 7, 8, 9 and 30 hours) samples were extracted, precipitated by TCA (trichloroacetic acid) and resuspended in a gel loading buffer containing 8 M Urea to eliminate further refolding in sample buffer. Samples were loaded onto Bis-Tris gels. After staining and destaining gels were photographed and band intensities were determined by densitometry using an AlphaDigDoc 1200 instrument.

Example 1: Δ21N^pro (HoBi)-pep6His

Refolding in Different Buffers in Presence of 2.5M Urea

Figure 1:
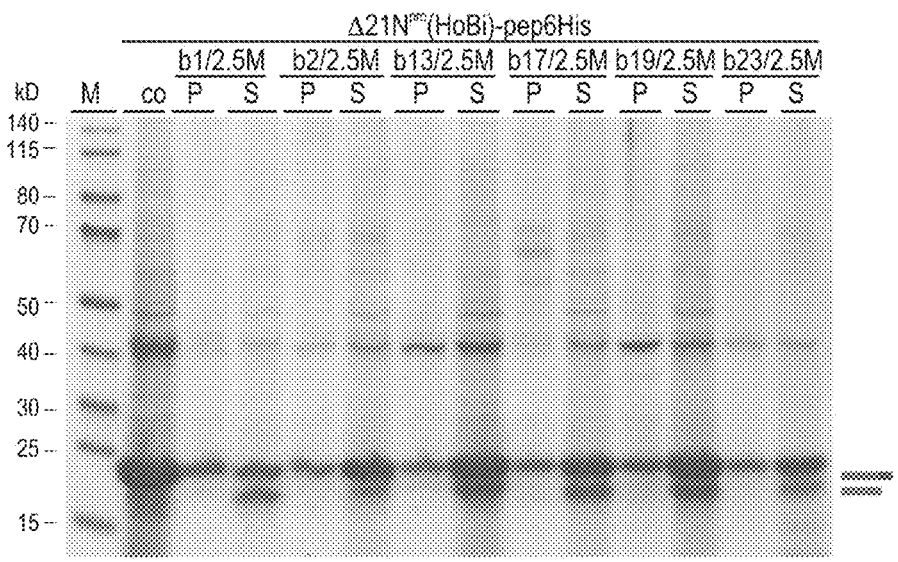
FIG. 1: SDS-PAGE of refolding of Δ21N$^{pro}$ (HoBi)-pep6His in five different refolding buffers containing 2.5M urea. 100 μl refolding batch (c=200 μg/ml) were centrifuged at 20,000×g. The supernatant was precipitated by TCA. Pellet and supernatant were resuspended in 10 μl 1× Magic Mix sample buffer and loaded onto NuPAGE® Bis-Tris 4-12% gels. As control the same amount of inclusion body was precipitated and analyzed. M . . . PageRuler™ Prestained Protein Ladder, P . . . pellet, S . . . supernatant, co . . . control, b . . . buffer. Amount of protein in PAGE samples: P and S together 20 μg.
Figure 2:
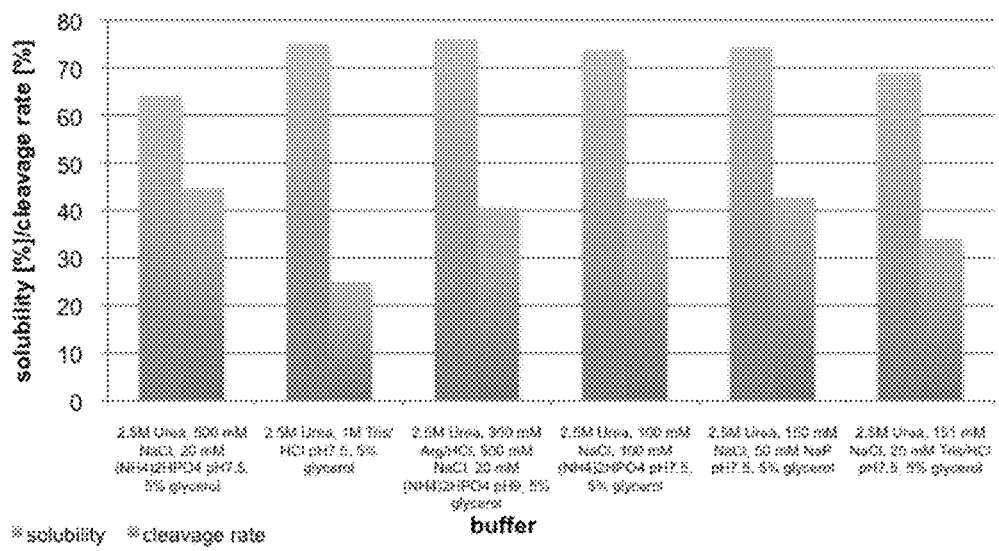
FIG. 2: Refolding efficiencies of D21N$^{pro}$ (HoBi)-pep6His in five different buffers in presence of 2.5M Urea. Gel was scanned in and band intensities were determined by densitometry using an AlphaDigDoc 1200 instrument.

Refolding studies revealed that Δ21N^pro (HoBi) was able to cleave off pep6His in presence of 2.5 M urea in all buffers with different efficiencies (FIG. 1 and FIG. 2).

Figure 3:
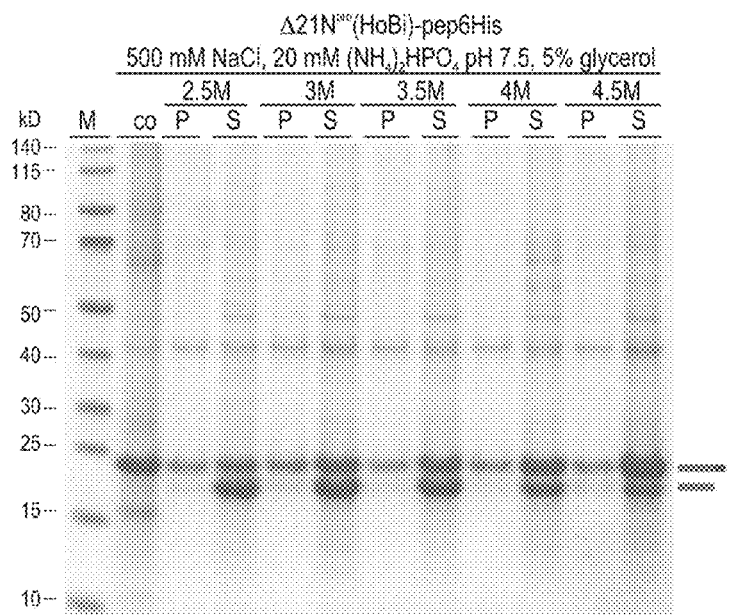
FIG. 3: Refolding of Δ21N$^{pro}$ (HoBi)-pep6His in 500 mM NaCl, mM (NH$_4$)$_2$HPO$_4$ pH 7.5, 5% glycerol with increasing Urea concentrations up to 4.5M. 100 μl refolding batch (c=200 μg/ml) were centrifuged at 20,000×g. The supernatant was precipitated by TCA. Pellet and supernatant were resuspended in 10 μl 1× Magic Mix sample buffer and loaded onto NuPAGE® Bis-Tris 4-12% gels. As control the same amount of inclusion body was precipitated and analyzed. M . . . PageRuler™ Prestained Protein Ladder, P . . . pellet, S . . . supernatant, co . . . control. Amount of protein in PAGE samples: P and S together 20 μg.
Figure 4:
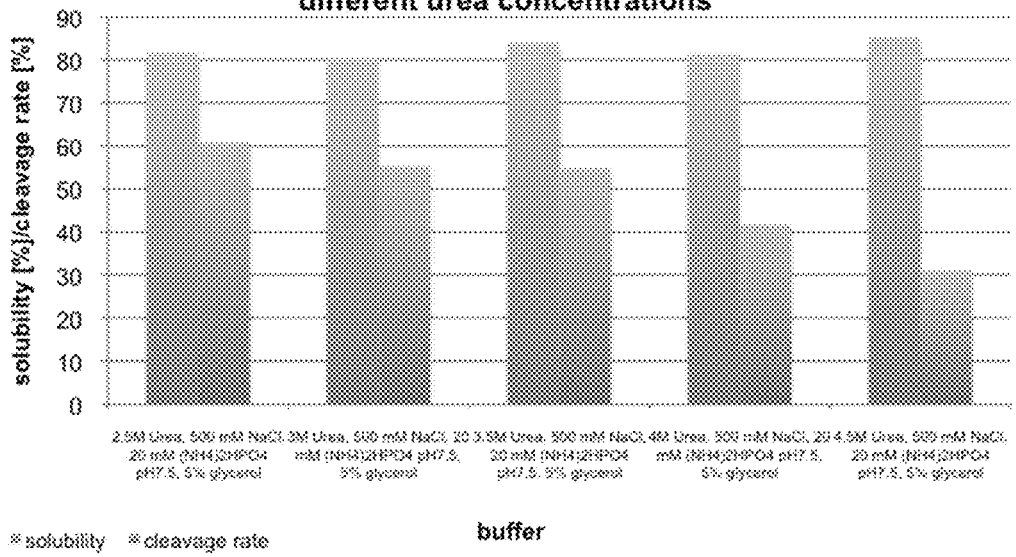
FIG. 4: Refolding efficiencies of Δ21N$^{pro}$ (HoBi)-pep6His in 500 mM NaCl, 20 mM (NH$_4$)$_2$HPO$_4$ pH 7.5, 5% glycerol with increasing Urea concentrations up to 4.5M. Gel was photographed and band intensities were determined by densitometry using an AlphaDigDoc 1200 instrument.

Refolding in 500 mM NaCl, 20 mM $(NH_4)_2HPO_4$ pH 7.5, 5% Glycerol Under Various Urea Concentrations SDS-PAGE shows that Δ21N^pro (HoBi) was able to cleave off pep6His at 4.5M urea (FIG. 3). Graph in FIG. 4 illustrates solubility and refolding efficiencies of Δ21N^pro (HoBi)-pep6His under different urea concentrations. It can be assumed that the higher the urea concentration the lower the refolding efficiency.

Figure 5A:
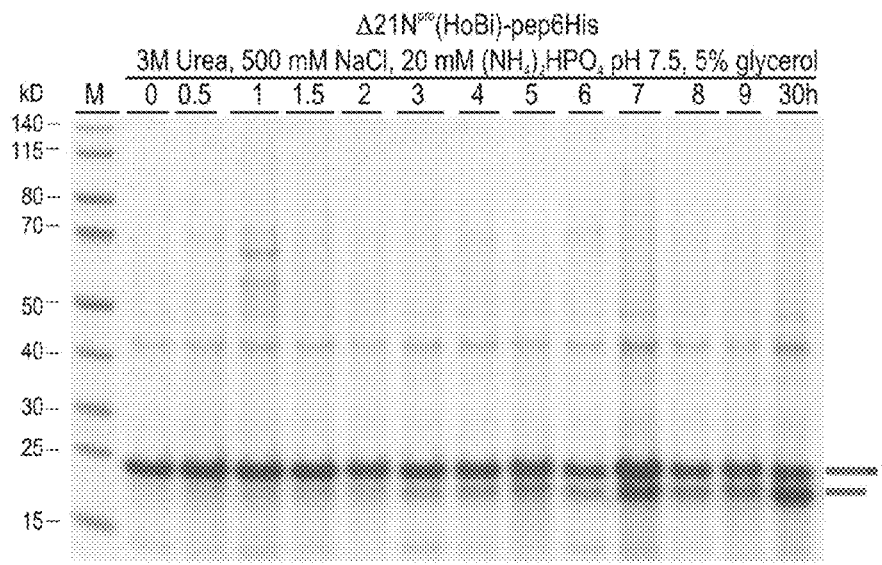
FIG. 5: Refolding of Δ21N$^{pro}$ (HoBi)-pep6His in 500 mM NaCl, 20 mM (NH$_4$)$_2$HPO$_4$ pH 7.5, 5% glycerol containing 3M (A), 3.5M (B) and 4M (C) Urea. Each time point 100 μl sample were extracted from the refolding batch (c=200 μg/ml) and precipitated by TCA. After resuspension in 10 μl 1× Magic Mix sample buffer samples were onto NuPAGE® Bis-Tris 4-12% gels. M . . . PageRuler™ Prestained Protein Ladder, P . . . pellet, S . . . supernatant, co . . . control, b . . . buffer. Amount of protein in each PAGE sample: 10 μg (A and C) and 5 μg (B).
Figure 5B:
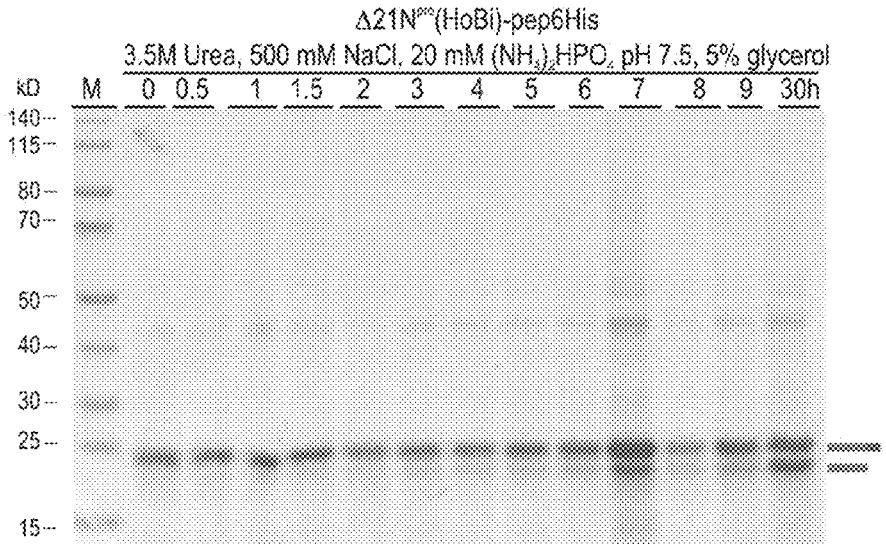
Figure 5C:
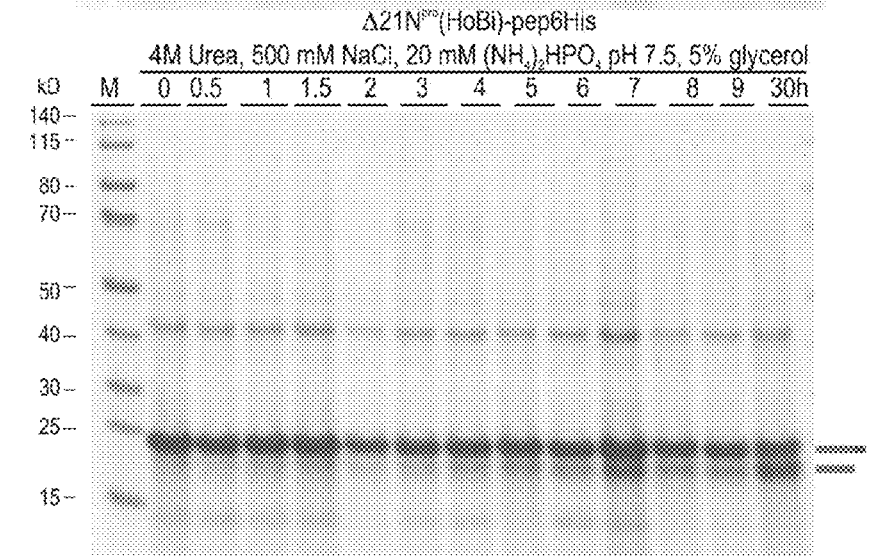
Figure 6:
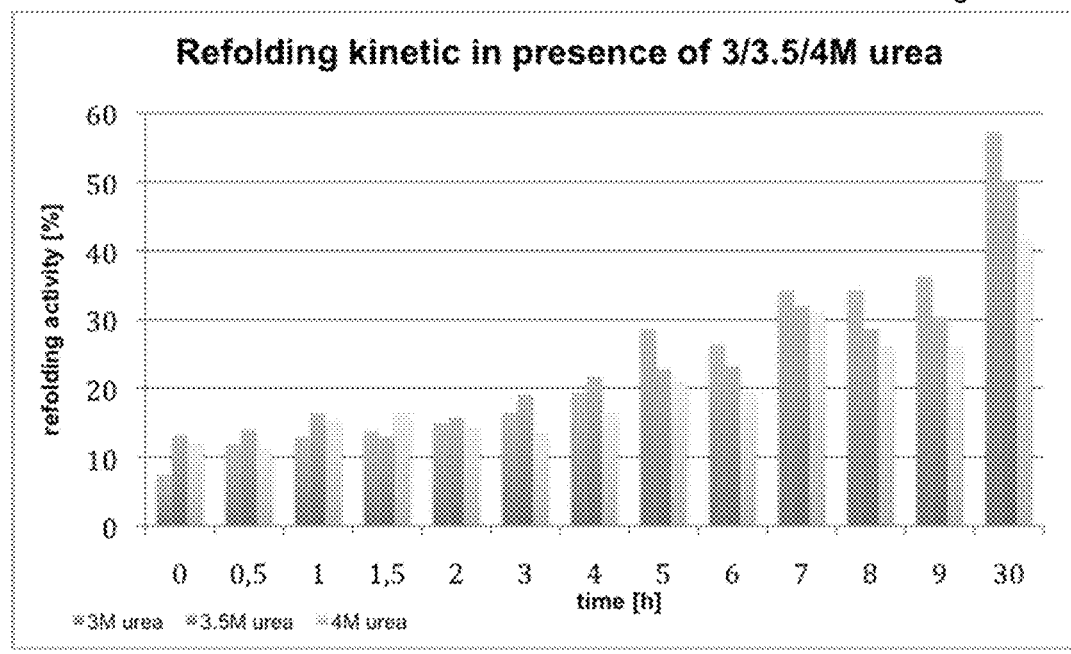
FIG. 6: Determination of the refolding kinetic of Δ21N$^{pro}$ (HoBi)-pep6His in 500 mM NaCl, 20 mM (NH$_4$)$_2$HPO$_4$ pH 7.5, 5% glycerol in presence of 3M, 3.5M and 4M Urea. Gels were photographed and band intensities were determined by densitometry using an AlphaDigDoc 1200 instrument.

Determination of the Refolding Kinetics in 500 mM NaCl, 20 mM $(NH_4)_2HPO_4$ pH 7.5, 5% Glycerol Under Three Different Urea Concentrations FIG. 5 shows the refolding kinetic of Δ21N^pro (HoBi)-pep6His in 500 mM NaCl, 20 mM $(NH_4)_2HPO_4$ pH 7.5, 5% glycerol at 3, 3.5 and 4M Urea. The higher the urea concentration, the slower the cleavage reaction took place (FIG. 6).

Example 2: Δ21N^pro (HOBi)-SDD-diUbi-pep6His

Refolding in Different Buffers in Presence of 2.5M Urea

Figure 7:
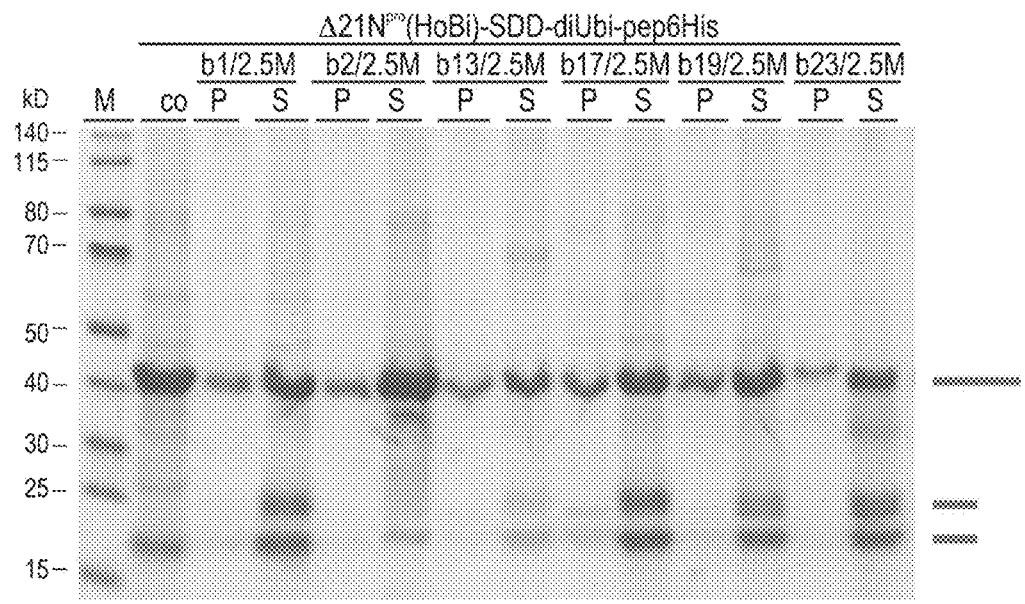
FIG. 7: SDS-PAGE of refolding of Δ21N$^{pro}$ (HOBi)-SDD-diUbi-pep6His in five different refolding buffers containing 2.5M urea. 100 μl refolding batch (c=200 μg/ml) were centrifuged at 20,000×g. The supernatant was precipitated by TCA. Pellet and supernatant were resuspended in 10 μl 1× Magic Mix sample buffer and loaded onto NuPAGE® Bis-Tris 4-12% gels. As control the same amount of inclusion body was precipitated and analyzed. M . . . PageRuler™ Prestained Protein Ladder, P . . . pellet, S . . . supernatant, co . . . control, b . . . buffer. Amount of protein in PAGE samples: P and S together 20 μg.

Analysis of refolding behavior of Δ21N^pro (HoBi)-SDD-diUbi-pep6His by SDS-PAGE showed that Δ21N^pro (HoBi) was able to cleave off SDD-diUbi-pep6His in presence of 2.5 M urea in majority of the buffers (except buffer 2 and buffer 13) with different efficiencies (FIG. 7). N-terminal sequencing determined that the band already visible in the control lane of Δ21N^pro (HoBi)-SDID-diUbi-pep6His at the molecular weight of approx. 18 kD derived from in vivo cleaved Δ21N^pro (HoBi). Determination of the refolding efficiency was left out of account due to the rather broad band of SDD-diUbi-pep6His.

Figure 8:
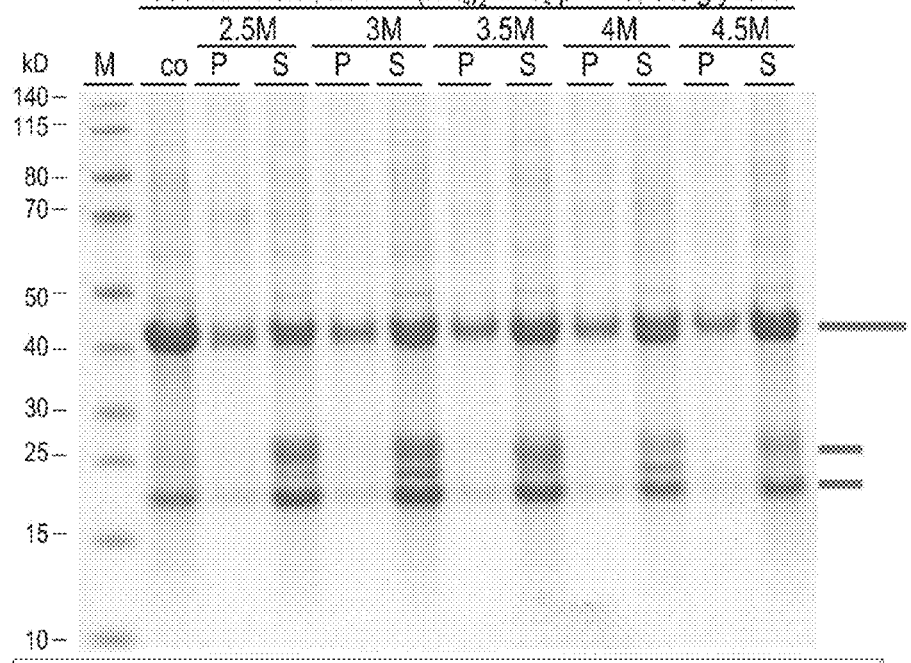
FIG. 8: Refolding of Δ21N$^{pro}$ (HoBi)-SDD-diUbi-pep6His in 500 mM NaCl, 20 mM (NH$_4$)$_2$HPO$_4$ pH 7.5, 5% glycerol with increasing Urea concentrations up to 4.5M. 100 μl refolding batch (c=200 μg/ml) were centrifuged at 20,000×g. The supernatant was precipitated by TCA. Pellet and supernatant were resuspended in 10 μl 1× Magic Mix sample buffer and loaded onto NuPAGE® Bis-Tris 4-12% gels. As control the same amount of inclusion body was precipitated and analyzed. M . . . PageRuler™ Prestained Protein Ladder, P . . . pellet, S . . . supernatant, co . . . control. Amount of protein in PAGE samples: P and S together 20 μg.

Refolding in 500 mM NaCl, 20 mM $(NH_4)_2HPO_4$ pH 7.5, 5% Glycerol Under Various Urea Concentrations SDS-PAGE in FIG. 8 illustrates that Δ21N^pro (HoBi)-SDD-diUbi-pep6His showed still cleavage activity 4.5M urea. Refolding efficiencies of Δ21N^pro (HoBi)-SDD-diUbi-pep6His were not calculated due to the rather broad band of the target protein SDD-diUbi-pep6His but it is visible that refolding efficiency decreases with raising urea concentration.

Example 3: Expression of D21N$^{pro}$ (HOBi)-MCP-1, SEQ.ID.NO. 4, and D21EDDIE-MCP-1, SEQ.ID.NO. 5 with *E. coli* in Fed Batch Mode Generation of Bacterial Strains and Description of Recombinant Proteins
Molecular Weights
MCP-1 (SEQ.ID.NO. 10): 8.7 kD
D21N$^{pro}$ (HoBi)-MCP-1 (SEQ.ID.NO. 4): 25.2 kD
D21EDDIE-MCP-1 (SEQ.ID.NO. 5): 25.3 kD
Sequences D21N$^{pro}$ (HoBi)-MCP-1 (SEQ.ID.NO. 4):
MEPLYDKNGAVLFGEPSDTHPQSTLKLPHPRGEDEVEVGIRDLPRKGDCRTGNRLGPVSGLFVK

PGPVFYQDYSGPVYHRAPLEQFKQTPMEETTKRIGRVTGSDGNLYHMYVETDGEILVKQAKREG

QDVLKWTYNTLDSPIWVTSCQPDAINAPVTCCYNFTNRKISVQRLASYRRITSSKCPKEAVIFK

TIVAKEICADPKQKWVQDSMDHLDKQTQTPKT

D21EDDIE-MCP-1 (SEQ.ID.NO. 5):
MEPVYDTAGRPLFGNPSEVHPQSTLKLPHDRGEDDIETTLRDLPRKGDCRSGNHLGPVSGIYIK

PGPVYYQDYTGPVYHRAPLEFFDETQFEETTKRIGRVTGSDGKLYHIYVEVDGEILLKQAKRGT

PRTLKWTRNTTNCPLWVTSCQPDAINAPVTCCYNFTNRKISVQRLASYRRITSSKCPKEAVIFK

TIVAKEICADPKQKWVQDSMDHLDKQTQTPKT

MCP-1 (SEQ.ID.NO. 10):
QPDAINAPVTCCYNFTNRKISVQRLASYRRITSSKCPKEAVIFKTIVAKEICADPKQKWVQDSM

DHLDKQTQTPKT

TABLE 1

| List of generated expression strains | | | |
|---|---|---|---|
| Protein | Strain | Plasmid | Promoter |
| D21N$^{pro}$(HoBi)-MCP-1 (SEQ. ID. NO. 4) | B121 (DE3) Novagen # 6950 | pET30a(+) from Novagen | T7 |
| D21EDDIE-MCP-1 (SEQ. ID. NO. 5) | B121 (DE3) Novagen # 6950 | pET30a(+) from Novagen | T7 |

Codon optimized genes of interest (GOIs) were synthesized (Geneart AG, Germany) and provided in the Geneart plasmids with an NdeI restriction site and an EcoRI restriction site as well as 2 TAA stop codons. The GOI DNAs obtained were digested with NdeI and EcoRI, and ligated into a pET30a vector (Novagen, Merck Millipore) restricted with the same enzymes.

For expression of Npro fragments *E. coli* strain BL21 (DE3) was used. *E. coli* BL21 (DE3) was transformed and grown o/n at 37° C.

3 clones were picked, resuspended in Luria-Bertani (LB) medium (Bertani, et al. 1951), grown at 37° C. until an optical density (OD550 nm) 0.2-0.5 and frozen as glycerol stock, all separately.

For expression evaluation clone screenings were performed: LB medium was inoculated from glycerol stock and grown overnight at 37° C. For the clone screening production culture LB medium was inoculated with a seed culture to an OD of 0.2, grown until OD 1. Subsequently, protein expression was induced by addition of 1 mM IPTG (Isopropyl β-D-1-thiogalactopyranoside) to the suspension. After incubation for 4 hours at 37° C., the cell pellets were harvested by centrifugation, stored at −20° C. and analyzed for productivity by SDS (Sodium Dodecyl sulfate) Page (Polyaclyamide gel electrophoresis) as follows:

Sample preparation: BugBuster Extraction Reagent (Novagen-Merck) plus Lysonase Bioprocessing Reagent mix (Novagen-Merck)
Gel: NuPage 12% Bis Tris, 1.0 mm (Invitrogen)
Sample buffer: NuPAGE LDS Sample Buffer (Invitrogen)
Reducing agent: 2-Mercaptoethanol (Sigma-Aldrich)
Running buffer: NuPAGE MES SDS Running Buffer (Invitrogen)
Detection: SimplyBlue SafeStain (Invitrogen)

Cultivation Mode and Process Analysis
Preculture 300 mL preculture medium (media composition as described in Example 4) in a glass shake flask were inoculated from a glycerol stock and grown until an optical density (OD550 nm) of 1.25 to 2.75 is reached.

Main Culture

The cells were grown in a 7 L (5 L net volume, 3 L batch volume) computer-controlled bioreactor (Sartorius Stedim Biotech AG, Germany) equipped with standard control units. The batch medium is described in Example 4 under "Media Composition". The pH is maintained at a set-point of 6.8±0.2 by addition of 25% ammonia solution (Merck), the temperature is set to 37° C.±0.5° C. and the aeration rate was fixed 5 L per minute. In order to avoid oxygen limitation, the dissolved oxygen level was stabilized above 20% saturation by stirrer speed and by enrichment with pure oxygen. The content of $O_2$ and $CO_2$ in the outlet air was determined by a photoacoustic multi-gas analyzer (Innova). Foaming was suppressed by addition of antifoam suspension (PPG 2000, Dow). For inoculation 30 ml preculture were transferred aseptically to the bioreactor. Feeding was started when the culture entered stationary phase. Fed-Batch regime with an exponential substrate feed was used to provide a constant growth rate of 0.25 $h^{-1}$ for 8.5 hours and afterwards the feed was changed to a constant mode at the actual feed rate. The feed medium is described in Example 4 under "Media Composition"

Induction

Induction was performed in a conventional mode by a single pulse directly into the bioreactor. The supplied amount of Isopropyl β-D-1-thiogalactopyranoside (IPTG) was calculated to set a concentration of 1 mM IPTG at the end of the process in order to gain a fully induced system.

Offline Analysis

Optical density (OD) was determined with a Genesis 10 spectrophotometer from Spectronic Instruments, USA, at 550 nm. The OD550 nm was measured in a range of 0.2-0.6. Above an extinction of 0.6 the samples were appropriately diluted with OD-buffer (20.7 g/L $Na_2HPO_4*12H_2O$, 5.7 g/L $KH_2PO_4$ and 11.6 g/L NaCl). Comparable culture broth dilutions as the measured OD-samples were filtered (pore size 0.2 μm) to generate blank values.

Bacterial dry matter (dry cell weights, DCW) was determined by centrifugation of 10 ml of the cell suspension, re-suspension in distilled water followed by centrifugation, and again re-suspension. Then the cell dry weight was determined using a Moisture analyzer ((Sartorius Stedim Biotech AG, Germany). Samples of 35 g culture broth were centrifuged. The supernatant was discarded, residual liquid removed and the weight of the biomass pellet determined.

Glucose in the culture supernatant was measured with the Glucose Analyzer YSI 2700 Select (Yellow Springs). The content of recombinant protein is determined by reducing SDS Page as follows:

Sample preparation: BugBuster Extraction Reagent (Novagen-Merck) plus Lysonase Bioprocessing Reagent mix (Novagen-Merck)
Gel: NuPage 12% Bis Tris, 1.0 mm (Invitrogen)
Sample buffer: NuPAGE LDS Sample Buffer (Invitrogen)
Reducing agent: 2-Mercaptoethanol (Sigma-Aldrich)
Running buffer: NuPAGE MES SDS Running Buffer (Invitrogen)
Detection: SimplyBlue SafeStain (Invitrogen)

Results

Both fusion proteins, $D21N^{pro}$ (HoBi)-MCP-1 (SEQ. ID.NO. 4) and D21EDDIE-MCP-1 (SEQ.ID.NO. 5), were expressed as insoluble Inclusion Bodies (IB) (FIGS. 9 and 10)

Figure 9:
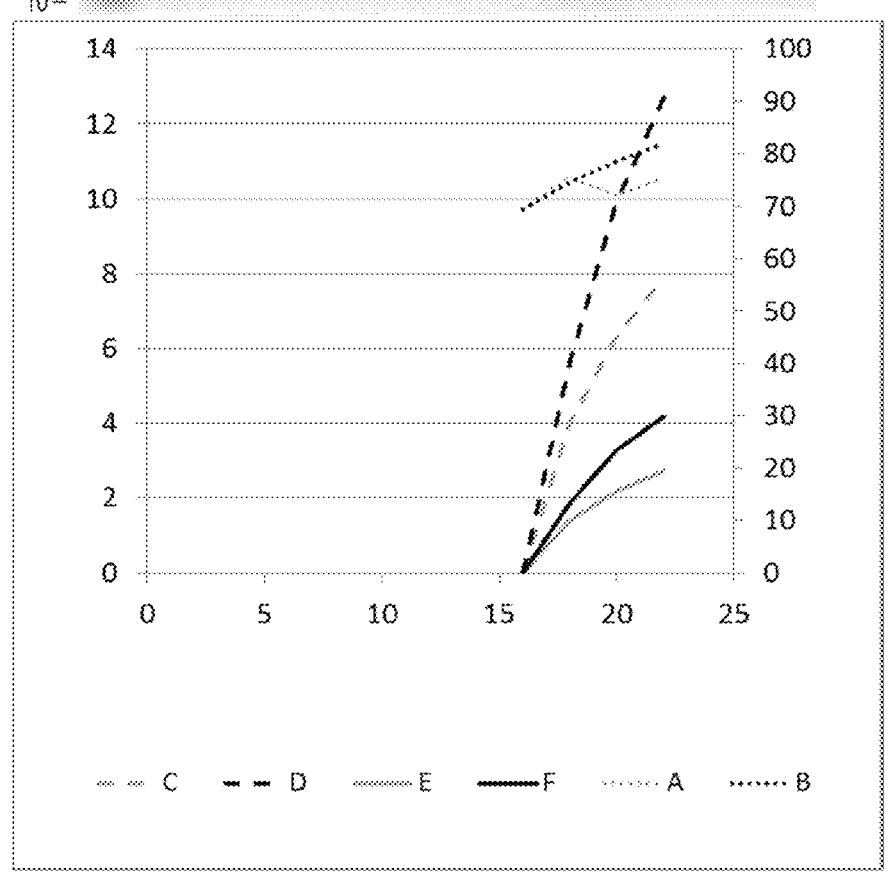
FIG. 9: Fermentation of. D21N$^{pro}$ (HoBi)-MCP-1 (SEQ. ID.NO. 4) and D21EDDIE-MCP-1 (SEQ.ID.NO. 5): Course of formation of biomass (DCW), titer of the fusion proteins and titer of MCP-1 (SEQ ID.NO. 10) within the fusion proteins x-axis stands for the feed time in [h]
left y-axis stands for the titer in [g/L]
right y-axis stands for the DCW (dry cell weight) in [g/L]
A: DCW of cells producing D21EDDIE-MCP-1 (SEQ. ID.NO. 5)
B: DCW of cells producing D21N$^{pro}$ (HoBi)-MCP-1 (SEQ. ID.NO. 4)
C: titer of D21EDDIE-MCP-1 (SEQ.ID.NO. 5)
D: titer of D21N$^{pro}$ (HoBi)-MCP-1 (SEQ.ID.NO. 4)
E: titer of MCP-1 within D21EDDIE-MCP-1 (SEQ.ID.NO. 5)
F: titer of MCP-1 within D21N$^{pro}$ (HoBi)-MCP-1 (SEQ. ID.NO. 4)
Figure 10:
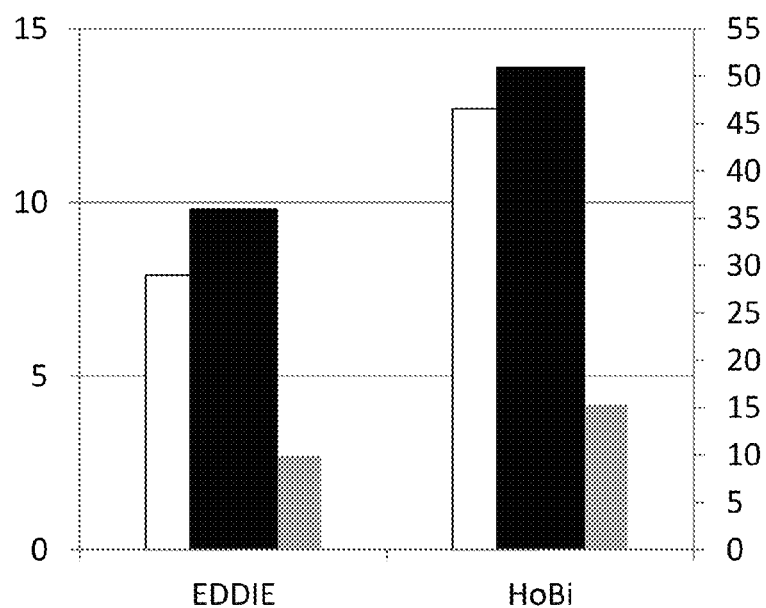
FIG. 10: Fermentation of. D21N$^{pro}$(HoBi)-MCP-1 (SEQ. ID.NO. 4) and D21EDDIE-MCP-1 (SEQ.ID.NO. 5): Comparison of the titer of the fusion proteins, the titer of MCP-1 within the fusion proteins and the specific titer of MCP-1

Summary:

FIGS. 9 and 10 clearly show, that the titer for MCP-1 (SEQ. ID. NO. 10) alone was significantly increased by expressing $D21N^{pro}$ (HoBi)-MCP-1 (SEQ.ID.NO. 4) compared to D21EDDIE-MCP-1 (SEQ.ID.NO. 5). The volumetric (g of MCP-1 per liter of culture broth) as well as the specific (mg of MCP-1 per g of cell dry weight, DCW) titer were increased 1.5- and 1.4-fold respectively Example 4: Refolding and Cleavage of Npro (HoBi) Fusion Proteins Compared to EDDIE Fusion Proteins with pep6His (SEQ.ID.NO. 11) and SOD-FLS (SEQ.ID.NO.12) as Fusion Partner Generation of Bacterial Strains and Description of Recombinant Proteins Experiments were performed with the B-strain BL21 (DE3) provided by Novagen. The designation (DE3) indicates that the hosts were lysogens of λ DE3 prophage, carrying a chromosomal copy of the T7 RNA polymerase gene under control of the lacUV5 promoter, making these strains suitable for protein expression using T7 or T7 lac promoters (Studier and Moffat, 1986; Studier et al., 1990). Expression of target proteins were performed with pET30a plasmid from Novagen (pET System manual, 11th edition).

TABLE 2

List of generated expression strains

| Protein | Strain | Plasmid | Promoter |
| --- | --- | --- | --- |
| D21Npro(HoBi)-pep6His (SEQ. ID. NO. 6) | BL21 (DE3) | pET30a | T7 |
| D21Npro(HoBi)-SOD-FLS (SEQ. ID. NO. 8) | BL21 (DE3) | pET30a | T7 |
| D21EDDIE-pep6His (SEQ. ID. NO. 7) | BL21 (DE3) | pET30a | T7 |
| D21EDDIE-SOD-FLS (SEQ. ID. NO. 9) | BL21 (DE3) | pET30a | T7 |

```
D21Npro(HoBi)-pep6His
                                                            (SEQ.ID.NO. 6)
MEPLYDKNGA  VLFGEPSDTH  PQSTLKLPHP  RGEKEVIVGI  RDLPRKGDCR

TGNRLGPVSG  LFVKPGPVFY  QDYSGPVYHR  APLEQFKQAP  MCEVTKRIGR

VTGSDGNLYH  MYVCTDGCIL  VKTAKREGQD  VLKWVYNVLD  SPIWVASCSV

DKLAAALEHH  HHHH

D21Npro(HoBi)-SOD-FLS
                                                            (SEQ.ID.NO. 8)
MEPLYDKNGA  VLFGEPSDTH  PQSTLKLPHP  RGEDEVEVGI  RDLPRKGDCR

TGNRLGPVSG  LFVKPGPVFY  QDYSGPVYHR  APLEQFKQTP  MEETTKRIGR

VTGSDGNLYH  MYVETDGEIL  VKQAKREGQD  VLKWTYNTLD  SPIWVTSCSV

MATKAVCVLK  GDGPVQGIIN  FEQKESNGPV  KVWGSIKGLT  EGLHGFHVHE

FGDNTAGCTS  AGPHFNPLSR  KHGGPKDEER  HVGDLGNVTA  DKDGVADVSI

EDSVISLSGD  HCIIGRTLVV  HEKADDLGKG  GNEESTKTGN  AGSRLACGVI

GTAQVDDYKD  DDDKGGGGSG  GGGSWSHPQF  EK

D21EDDIE-SOD-FLS
                                                            (SEQ.ID.NO. 9)
MEPVYDTAGR  PLFGNPSEVH  PQSTLKLPHD  RGEDDIETTL  RDLPRKGDCR

SGNHLGPVSG  IYIKPGPVYY  QDYTGPVYHR  APLEFFDETQ  FEETTKRIGR

VTGSDGKLYH  IYVEVDGEIL  LKQAKRGTPR  TLKWTRNTTN  CPLWVTSCDT
```

-continued

```
MATKAVCVLK GDGPVQGIIN FEQKESNGPV KVWGSIKGLT EGLHGFHVHE

FGDNTAGCTS AGPHFNPLSR KHGGPKDEER HVGDLGNVTA DKDGVADVSI

EDSVISLSGD HCIIGRTLVV HEKADDLGKG GNEESTKTGN AGSRLACGVI

GTAQVDDYKD DDDKGGGGSG GGGSWSHPQF EK
```

D21EDDIE-pep6His (SEQ.ID.NO. 7)
```
MEPVYDTAGR PLFGNPSEVH PQSTLKLPHD RGEDDIETTL RDLPRKGDCR

IYIKPGPVYY QDYTGPVYHR APLEFFDETQ FEETTKRIGR VTGSDGKLYH

IYVEVDGEIL LKQAKRGTPR TLKWTRNTTN CPLWVTSCDT SVDKLAAALE HHHHHH
```

Pep6His (SEQ.ID.NO. 11)
```
SV DKLAAALEHH HHHH
```

SOD-FLS (SEQ.ID.NO. 12)
```
SV MATKAVCVLK GDGPVQGIIN FEQKESNGPV KVWGSIKGLT EGLHGFHVHE

FGDNTAGCTS AGPHFNPLSR KHGGPKDEER HVGDLGNVTA DKDGVADVSI

EDSVISLSGD HCIIGRTLVV HEKADDLGKG GNEESTKTGN AGSRLACGVI

GTAQVDDYKD DDDKGGGGSG GGGSWSHPQF EK
```

Cultivation Mode and Process Analysis

The cells were grown in a 10 L (5 L working volume) computer-controlled bioreactor (MBR; Wetzikon, CH) equipped with standard control units. The pH is maintained at a set-point of 7.0±0.05 by addition of 25% ammonia solution (ACROS Organics), the temperature was set to 37° C.±0.5° C. In order to avoid oxygen limitation, the dissolved oxygen level was stabilized above 30% saturation by stirrer speed and aeration rate control. The content of $O_2$ and $CO_2$ in the outlet air was determined by a Hartmann and Braun Advanced Optima gas analyzer. Dielectric capacity and conductivity were measured with the Biomass monitor, model 214M (Aber Instruments, Aberystwyth, UK) set. Foaming was suppressed by addition of antifoam suspension (PPG2000, Bussetti, Vienna) with a concentration of 0.5 ml/l feed medium. For inoculation, a deep frozen (−80° C.) working cell bank vial, was thawed and 1 ml (optical density $OD_{600}=1$) was transferred aseptically to the bioreactor. Feeding is started when the culture, grown to a bacterial dry matter of 7.5 g in 4.0 L batch medium, entered stationary phase. Fed-Batch regime with an exponential substrate feed was used to provide a constant growth rate of $0.2$ $h^{-4}$ during 2 doubling times. The substrate feed was controlled by increasing the pump speed according to the exponential growth algorithm, $x=x_o \cdot e^{\mu t}$, with superimposed feedback control of weight loss in the substrate tank (Cserjan-Puschmann et al., 1999). The feed medium provided sufficient components to yield 129 g of bacterial dry matter.

Induction

Induction was performed in a conventional mode by a single pulse directly into the bioreactor. The supplied amount of IPTG was calculated to set a concentration of 20 µmol IPTG/g CDM at the end of the process in order to gain a fully induced system.

Media Composition

The minimal medium used in this study contained 3 g $KH_2PO_4$ and 6 g $K_2HPO_4 \cdot 3H_2O$ per liter. These concentrations provide the required buffer capacity and serve as P and K source as well. The other components were added in relation of gram bacterial dry matter to be produced: sodium citrate (trisodium salt*$2H_2O$; ACROS organics) 0.25 g, $MgSO_4 \cdot 7H_2O$ 0.10 g, $CaCl_2 \cdot 2H_2O$ 0.02 g, trace element solution 50 µl and glucose*$H_2O$ 3 g. To accelerate initial growth of the population, the complex component yeast extract 0.15 g is added to the minimal medium to obtain the batch medium. For the feeding phase 1 L of minimal medium are prepared according to the amount of biological dry matter 129 g to be produced in the feeding phase, whereby P-salts are again added per liter. Trace element solution: prepared in 5 N HCl (g/L): $FeSO_4 \cdot 7H_2O$ 40.0, $MnSO_4 \cdot H_2O$ 10.0, $AlCl_3 \cdot 6H_2O$ 10.0, $CoCl_2$ (Fluka) 4.0, $ZnSO_4 \cdot 7H_2O$ 2.0, $Na_2MoO_2 \cdot 2H_2O$ 2.0, $CuCl_2 \cdot 2H_2O$ 1.0, $H_3BO_3$ 0.50.

Offline Analysis

Optical density (OD) was measured at 600 nm. Bacterial dry matter was determined by centrifugation of 10 ml of the cell suspension, re-suspension in distilled water followed by centrifugation, and re-suspension for transfer to a pre-weighed beaker, which was then dried at 105° C. for 24 h and re-weighed. The progress of bacterial growth was determined by calculating the total amount of biomass (total bacterial dry matter BDM; also termed cell dry weight CDW).

The quantification of the expressed fusion protein as illustrated in FIG. 11 was performed with SDS-PAGE by means of a linear regression curve of a reference. Therefore, the samples of solubilized IBs were diluted to be within the calibration range and protein content of bands was determined densitometrically by the ImageQuantTL Software.

Expression systems listed in Table 2 are used to produce the fusion proteins of D21N$^{pro}$ (Hobi) and D21EDDIE with pep6His (SEQ.ID.NO. 11) and SOD-FLS (SEQ.ID.NO. 12 as fusion partners to compare the cleavage properties of the two autoprotease variants under different refolding conditions. Induction is performed as single pulse one doubling past feed start in order to gain a fully induced system.

TABLE 3

Production of D21N$^{pro}$(HoBi)-pep6His (SEQ ID No. 6), D21N$^{pro}$(HoBi)-SOD-FLS (SEQ ID No. 8), D21EDDIE-pep6His (SEQ ID No. 7), and D21EDDIE-SOD-FLS (SEQ ID No. 9)

|  | D21N$^{pro}$ (HoBi)- pep6His SEQ ID NO. 6 | A21N$^{pro}$ (HoBi)- SOD-FLS SEQ ID No. 8 | A21EDDIE- pep6His SEQ ID No. 7 | A21EDDIE- SOD-FLS SEQ ID NO. 9 |
|---|---|---|---|---|
| Total yield of bacterial dry matter (DCW) [g] | 126 | 123 | 131 | 131 |

Cserjan-Puschmann, M.; Kramer, W.; Dürrschmid, E.; Striedner, G.; Bayer, K. *Metabolic approaches for the optimisation of recombinant fermentation processes.* Appl. Microbiol. Biotechnol, 1999, 53, 43-50.

Studier, F. W., and Moffatt, B. A. *Use of the bacteriophage T7 RNA polymerase to direct selective high-level expression of cloned genes.* J. Mol. Biol., 1986, 189, 113-130.

Studier, F. W.; Rosenberg, A. L.; Dunn, J. J.; Dubendorff, J. W. *Use of T7 RNA polymerase to direct expression of cloned genes.* Meth. Enzym., 1990, 185, 60-89.

Preparation of Inclusion Bodies (IB)

The IBs of the above mentioned proteins were harvested as described previously (Walter et al., 2013). The wet cell paste was harvested using a disk centrifuge (Pathfinder PSC 1-06-177; GEA GEA Westfalia Separator Group, Oelde, Germany) and re-suspended in 50 mM Tris, 50 mM NaCl, and 0.02% Tween at pH 8.0 using an ultra turrax (IKA, Staufen, Germany) to obtain a dry matter concentration of 30 g/L. The slurry was passed twice through a Panda 2K homogenizer (GEA Niro Soavi S.p.A., Italy) at a pressure of 1000 bar. IBs were separated using a disk centrifuge, and the resulting pellet was washed twice with 20 mM Tris, 0.5 M NaCl, and 0.02% Tween at pH 8.0. After centrifugation, the pellet was re-suspended using the ultra turrax and washed once with 0.5 M NaCl. After each washing step, the IBs were separated using the disk centrifuge. The final pellet was re-suspended in water to obtain a 40% IB suspension and stored at −20° C. Prior to the experiments, the IBs were lyophilized and stored at 4° C.

C. Walther, S. Mayer, A. Trefilov, G. Sekot, R. Hahn, A. Jungbauer, A. Dürauer, (2013): *Prediction of Inclusion Body Solubilzation From Shaken to Stirred Reactors,* Biotechnology & Bioengineering, 111: 84-94

Solubilization of Inclusion Bodies (IB)

The IBs solubilization was carried out as described previously (Walther et al., 2013). For solubilization of IB proteins, lyophilized IBs were resuspended in water for 1 h. The IB suspension was dissolved at a ratio of 1:10 in the corresponding solubilization buffer. The concentration of buffer ingredients was adjusted taking the dilution factor of IB suspension into account to achieve resulting urea concentrations of 8 M or 4 M and 5M GuHCl, respectively. Additionally, the solubilization buffers contained final concentration 50 mM Tris and 100 mM MTG at a pH 7.3. After 2 h, solubilization in the reactor was stopped by at 13,200 rpm at 21° C. for 5 min (Centrifuge 5415R, Eppendorf, Germany) and consecutive filtration through 0.22-μm filters (Millipore, Billerica, Mass., USA).

C. Walther, S. Mayer, A. Trefilov, G. Sekot, R. Hahn, A. Jungbauer, A. DÜrauer, (2013): *Prediction of Inclusion Body Solubilization From Shaken to Stirred Reactors,* Biotechnology & Bioengineering, 111: 84-94

Refolding and Cleavage

Refolding was carried out by rapid dilution of the solubilized IBs into refolding buffer in the ratio 1:20 keeping either the residual concentration of the chaotrope constant for all experiments and varying the protein concentration or vice versa. As refolding buffers two compositions were used as listed in Table 4.

TABLE 4

Buffer compositions used for refolding

| Name | Shortcut | Composition | pH |
|---|---|---|---|
| TRIS buffer | Tris | 1M Tris, 0.25M sucrose, 2 mM EDTA, 20 mM MTG | 7.3 |
| Ammonium phosphate buffer | Am-Ph | 20 mM ammonium phosphate, 5% glycerol, 20 mM MTG | 7.5 |

Determination of the Cleavage Yield [%]

The analysis of the cleavage yield was carried out as described previously (Walther et al., 2013). The cleavage yield was determined analyzing aliquots of the refolding samples throughout the renaturation process over time by RP-HPLC. Separation of the fusion protein from the cleaved target and autoprotease enables the calculation of the cleaving yield via the increase of the cleaved target/autoprotease compared to the initial overall fusion protein.

RP-HPLC was performed using a TSKgel Super-Octyl column (4.6×50/100 mm, 2 μm, 110 Å) (Tosoh Bioscience, Germany). The buffer system consisted of 0.1% (v/v) trifluoroacetic acid (TFA) in water as buffer A and 0.1% (v/v) TFA in acetonitrile as buffer B. Solubilization and refolding samples were injected directly. Elution was performed using different gradients that were optimized for each fusion protein that was analyzed. Detection proceeded at two wavelengths, 214 nm and 280 nm, to distinguish between proteins and buffer components. Calibration curves were established for all fusion proteins to quantify the protein in solution.

C. Walther, S. Mayer, A. Trefilov, G. Sekot, R. Hahn, A. Jungbauer, A. Dürauer, (2013): *Prediction of Inclusion Body Solubilzation From Shaken to Stirred Reactors,* Biotechnology & Bioengineering, 111: 84-94

Results

Cleavage Kinetic of D21N$^{pro}$ (HoBi)-SOD-FLS (SEQ. ID.NO. 8) Compared to D21EDDIE-SOD-FLS (SEQ. ID.NO. 9) at Different Urea Concentrations:

The IBs were solubilized in 8M Urea and refolded in two different refolding buffers, Tris and AmPh in presence of increasing concentration of Urea. The protein concentration was identical for all experiments, i.e. c=0.1 mg/mL.

Figure 12A:
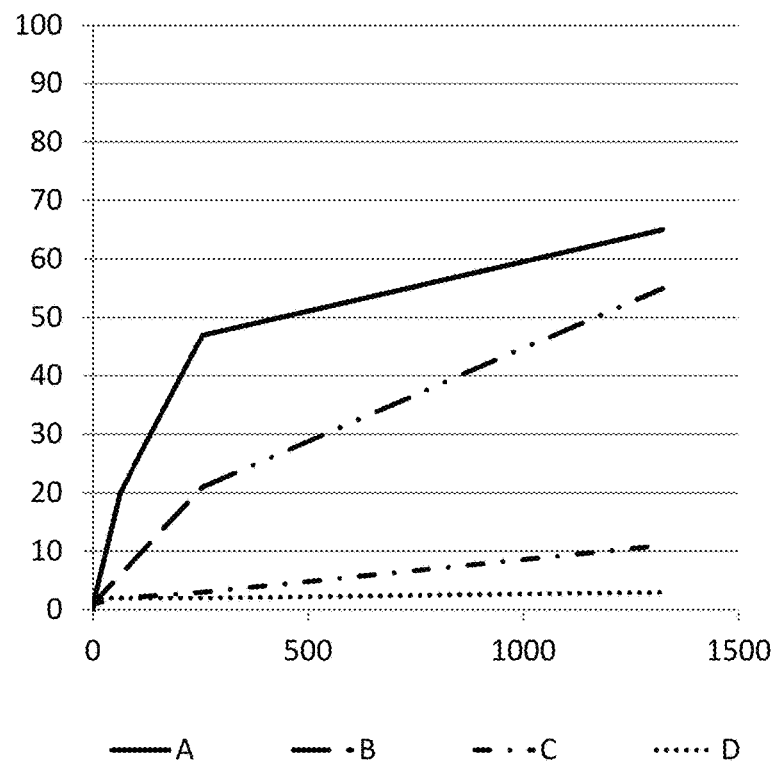
Figure 12B:
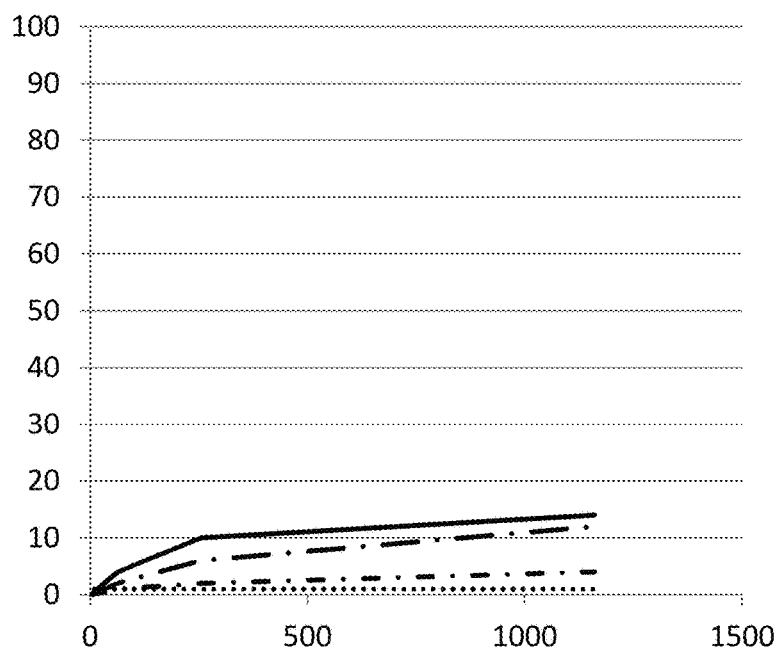

FIG. 12 shows that cleavage kinetic and yield is superior for D21N$^{pro}$ (HoBi)-SOD-FLS (SEQ.ID.NO. 8), when refolded in Tris buffer. The cleavage yield after 24 hours, when refolded in AmPh was also superior for D21N$^{pro}$ (HoBi)-SOD-FLS (SEQ.ID.NO. 8)(Table 5).

TABLE 5

Cleavage yield of D21N^pro(HoBi)-SOD-FLS (SEQ. ID. NO. 8) compared to D21EDDIE-SOD-FLS (SEQ. ID. NO. 9) at different Urea concentrations, when refolded in Am—Ph:

| N^pro variant | D21Npro(HoBi)-SOD-FLS (SEQ. ID. NO. 8) | | | | D21EDDIE-SOD-FLS (SEQ. ID. NO. 9) | | | |
|---|---|---|---|---|---|---|---|---|
| Solubilization buffer/Refolding buffer | 8M Urea/Am—Ph | | | | | | | |
| Residual Urea concentration (M) | 0.4 | 1 | 2 | 3 | 0.4 | 1 | 2 | 3 |
| Cleavage yield (%) | 66 | 21 | 6 | 3 | 7 | 5 | 0 | 0 |

Cleavage Yield of D21Npro (HoBi)-pep6His (SEQ.ID.NO. 6) Compared to D21EDDIE-pep6His (SEQ.ID.NO. 7) at Different Urea Concentrations:

The IBs were solubilized in 8M Urea or 5 M GuHCl and refolded in two different refolding buffers, Tris and AmPh in presence of increasing concentration of Urea or GuHCl. The protein concentration was identical for all experiments, i.e. c=0.1 mg/mL.

TABLE 6

Cleavage yield after 24 hours of D21^Npro(HoBi)-pep6His (SEQ. ID. NO. 6) compared to D21EDDIE-pep6His (SEQ. ID. NO. 7) in Tris buffer or Am—Ph buffer buffer after solubilization in 8M Urea or 5M GuHCl in presence of increasing concentration of residual chaotrope at the constant protein concentrations of 0.1 mg/mL.

| Variant | D21Npro(HoBi)-pep6His (SEQ. ID. NO. 6) | | | | D21EDDIE-pep6His (SEQ. ID. NO. 7) | | | |
|---|---|---|---|---|---|---|---|---|
| Solubilization/Refolding buffer | 8M Urea/Tris | | | | | | | |
| Residual Urea Concentration (M) | 0.4 | 1 | 2 | 3 | 0.4 | 1 | 2 | 3 |
| Cleavage Yield (%) after 24 h | 80 | 80 | 64 | 34 | 67 | 55 | 41 | 0 |
| Solubilization/Refolding buffer | 8M Urea/Am—Ph | | | | | | | |
| Residual Urea Concentration (M) | 0.4 | 1 | 2 | 3 | 0.4 | 1 | 2 | 3 |
| Cleavage Yield (%) after 24 h | prec | 68 | 42 | 12 | n.d. | n.d. | n.d. | n.d. |
| Solubilization/Refolding buffer | 5M GuHCL/Tris | | | | | | | |
| Residual Urea Concentration (M) | 0.25 | 0.5 | 1 | 1.5 | 0.25 | 0.5 | 1 | 1.5 |
| Cleavage Yield (%) after 24 h | 74 | 63 | 23 | 65 | n.d. | n.d. | n.d. | n.d. |
| Solubilization/Refolding buffer | 5M GuHCL/Am—Ph | | | | | | | |
| Residual Urea Concentration (M) | 0.25 | 0.5 | 1 | 1.5 | 0.25 | 0.5 | 1 | 1.5 |
| Cleavage Yield (%) after 24 h | 67.5 | 55 | 23 | prec | n.d. | n.d. | n.d. | n.d. | n.d. . . . not determined

Summary:

The D21N^pro (HoBi) autoprotease activity in increasing concentrations of chaotrop was for both proteins of interest (pep6His, SEQ.ID.NO. 11 and SOD-FLS, SEQ.ID.NO. 12) and in different refolding buffers (FIG. 12, Table 5 and Table 6) superior compared to the D21EDDIE autoprotease.

The invention claimed is:

1. Method for producing a recombinant protein of interest, which comprises:
   (a) providing a fusion protein comprising an N$^{pro}$ autoprotease moiety and a protein of interest moiety in inclusion bodies,
   (b) solubilising the inclusion bodies,
   (c) allowing the fusion protein to be cleaved by the N$^{pro}$ autoprotease moiety under chaotropic conditions, wherein the chaotropic conditions correspond to a urea concentration of 2 to 5 M urea, wherein the recombinant protein of interest is cleaved from the fusion protein and wherein the recombinant protein of interest is not yet renatured or simultaneously renatured, and
   (d) recovering the protein of interest, optionally including a renaturing step for the protein of interest,
   wherein the N$^{pro}$ autoprotease moiety consists of the sequence set forth by SEQ ID NO: 1.

2. The method according to claim 1, wherein the inclusion bodies were generated in a recombinant production system.

3. The method according to claim 1, wherein the conditions in step (b) correspond to a urea concentration of more than 5 M.

4. The method according to claim 1, wherein the chaotropic conditions in step (c) correspond to a urea concentration of from 2 to 4 M.

5. The method according to claim 1, wherein the $N^{pro}$ autoprotease moiety has a 24 h cleavage rate at 2.5 M urea of at least 20%.

6. The method according to claim 1, wherein the protein of interest is a protein for therapeutic use in humans.

7. The method according to claim 1, wherein step (b) and/or step (c) is performed at a pH of 5 to 11.

8. The method according to claim 1, wherein step (b) is performed under basic pH conditions.

9. The method according to claim 1, wherein the renaturing step for the protein of interest is carried out after recovery of the protein of interest.

10. The method according to claim 1, wherein the fusion protein comprises additional moieties.

11. The method according to claim 1, wherein the fusion protein is at least partially purified between step (b) and step (c).

12. The method according to claim 1, wherein the fusion protein is at least partially purified between step (b) and step (c) by affinity purification.

13. The method according to claim 1, wherein in step (b) is performed in the presence of guanidinium hydrochloride at a concentration of more than 2.5 M.

14. The method according to claim 1, wherein in step (c) is performed in the presence of guanidinium hydrochloride at a concentration of from 0.7 to 2.5 M.

15. The method according to claim 2, wherein the recombinant production system is a prokaryotic host cell.

16. The method according to claim 2, wherein the recombinant production system is *E. coli* host cells.

17. The method according to claim 3, wherein the urea concentration in step (b) is more that 6 M.

18. The method according to claim 17, wherein the urea concentration in step (b) is more that 7.5 M.

19. The method according to claim 5, wherein the $N^{pro}$ autoprotease moiety has a 24 h cleavage rate at 2.5 M urea of at least 30%.

20. The method according to claim 19, wherein the $N^{pro}$ autoprotease moiety has a 24 h cleavage rate at 2.5 M urea of at least 40%.

21. The method according to claim 6, wherein the protein of interest is a human recombinant protein or a vaccination antigen.

22. The method according to claim 7, wherein step (b) and/or step (c) is performed at a pH of 6 to 9.5.

23. The method according to claim 22, wherein step (b) and/or step (c) is performed at a pH of 6.5 to 8.5.

24. The method according to claim 11, wherein step (b) is performed in the presence of more than 5 mM NaOH or KOH.

25. The method according to claim 24, wherein step (b) is performed in the presence of more than 25 mM NaOH or KOH.

26. The method according to claim 25, wherein step (b) is performed in the presence of more than 100 mM NaOH or KOH.

27. The method according to claim 1, wherein the renaturing step for the protein of interest is carried out after recovery of the protein of interest.

28. The method according to claim 10, wherein the fusion protein comprises an affinity tag or a refolding aid moiety.

29. The method according to claim 10, wherein the additional moieties is selected from the group consisting of His-tag, SlyD, oligo amino acid stretches composed of either positive or negative charged moieties, Strep-tag and FLAG-tag.

30. The method according to claim 12, wherein the fusion protein is at least partially purified between step (b) and step (c) by affinity chromatography or affinity precipitation.

31. The method according to claim 13, wherein in step (b) is performed in the presences of guanidinium hydrochloride at a concentration of more than 3 M.

32. The method according to claim 31, wherein in step (b) is performed in the presence of guanidinium hydrochloride at a concentration of more than 3.75 M.

33. The method according to claim 14, wherein in step (c) is performed in the presence of guanidinium hydrochloride at a concentration of from 1 to 2 M.

34. The method according to claim 10, wherein the fusion protein is purified between step (b) and step (c).

35. The method according to claim 11, wherein the fusion protein is purified between step (b) and step (c) by affinity purification.

36. The method according to claim 12, wherein the fusion protein is purified between step (b) and step (c) by affinity chromatography.

* * * * *